(12) United States Patent
Glenn, Jr. et al.

(10) Patent No.: US 7,640,050 B2
(45) Date of Patent: Dec. 29, 2009

(54) SYSTEM AND METHOD FOR ANALYZING AND DISPLAYING COMPUTED TOMOGRAPHY DATA

(75) Inventors: William V. Glenn, Jr., Manhattan Beach, CA (US); Roger Kemper, Los Angeles, CA (US)

(73) Assignee: Netkiser, Inc., Manhattan Beach, CA (US)

( * ) Notice: Subject to any disclaimer, the term of this patent is extended or adjusted under 35 U.S.C. 154(b) by 558 days.

(21) Appl. No.: 10/507,337

(22) PCT Filed: Mar. 14, 2003

(86) PCT No.: PCT/US03/07996

§ 371 (c)(1),
(2), (4) Date: Apr. 25, 2005

(87) PCT Pub. No.: WO03/077758

PCT Pub. Date: Sep. 25, 2003

(65) Prior Publication Data

US 2005/0245803 A1 Nov. 3, 2005

Related U.S. Application Data

(60) Provisional application No. 60/364,269, filed on Mar. 14, 2002, provisional application No. 60/429,827, filed on Nov. 27, 2002.

(51) Int. Cl.
*A61B 5/05* (2006.01)
*G06K 9/00* (2006.01)
(52) U.S. Cl. .................. 600/407; 382/128; 600/425

(58) Field of Classification Search .................. 600/478, 600/407, 415, 425; 382/128; 378/4
See application file for complete search history.

(56) References Cited

U.S. PATENT DOCUMENTS

| | | | |
|---|---|---|---|
| 4,998,972 A | 3/1991 | Chin et al. | |
| 5,359,637 A | 10/1994 | Webber | |
| 5,381,786 A | 1/1995 | Spears | |
| 5,469,353 A | 11/1995 | Pinsky et al. | |
| 5,513,101 A | 4/1996 | Pinsky et al. | |
| 5,655,084 A | 8/1997 | Pinsky et al. | |
| 5,699,798 A | 12/1997 | Hochman et al. | |
| 5,734,384 A * | 3/1998 | Yanof et al. | 345/424 |
| 5,782,762 A | 7/1998 | Vining | |

(Continued)

FOREIGN PATENT DOCUMENTS

JP 200051207 A1 2/2000

OTHER PUBLICATIONS

A. Vilanova Bartroli et al., "Virtual Colon Flattening", May 2001, VisSym '01 Joint Eurographics—IEEE TCVG Symposium on Visualization, Conference Proceedings, pp. 127-136.*

(Continued)

*Primary Examiner*—Eric F Winakur
*Assistant Examiner*—Katherine L Fernandez
(74) *Attorney, Agent, or Firm*—Fulwider Patton LLP

(57) ABSTRACT

A system (10) and method are provided for analyzing and displaying images rendered from data sets resulting from a scan of a patient. The images displayed include both two-dimensional and three-dimensional views of selected portions of a patient's anatomy, for example, a tubular structure such as a colon.

10 Claims, 12 Drawing Sheets

U.S. PATENT DOCUMENTS

| | | | |
|---|---|---|---|
| 5,854,850 A * | 12/1998 | Linford et al. | 382/128 |
| 5,891,030 A | 4/1999 | Johnson et al. | |
| 5,920,319 A * | 7/1999 | Vining et al. | 345/420 |
| 6,081,577 A | 6/2000 | Webber | |
| 6,083,162 A | 7/2000 | Vining | |
| 6,201,988 B1 | 3/2001 | Bourland et al. | |
| 6,212,420 B1 * | 4/2001 | Wang et al. | 600/407 |
| 6,266,161 B1 | 7/2001 | Hara | |
| 6,272,366 B1 | 8/2001 | Vining | |
| 6,283,918 B1 | 9/2001 | Kanda et al. | |
| 6,289,235 B1 | 9/2001 | Webber et al. | |
| 6,349,373 B2 | 2/2002 | Sitka et al. | |
| 6,366,800 B1 | 4/2002 | Vining et al. | |
| 6,381,029 B1 | 4/2002 | Tipimeni | |
| 6,381,557 B1 | 4/2002 | Babula et al. | |
| 6,466,683 B1 | 10/2002 | Poor | |
| 6,510,340 B1 | 1/2003 | Jordan | |

OTHER PUBLICATIONS

Bartrolli et al., "Virtual Colon Flattening," http://www.tiani.com/research/Colon Flattening/animation, 2pgs, Jan. 27, 2003.

Point Dx, Inc., Grouping of Web pages, "Our Products," http://pointdx.com/ourProducts.php, Feb. 3, 2003.

Boston University School of Medicine, "Third International Symposium Virtual Colonoscopy," Apr. 8-10, 1992, pp. 1-144, Boston, MA.

Viatronix, Inc., "Viatronix, V3D—The new imaging reality," (Company Brochure), undated.

Bartroli et al., "Nonlinear Virtual Colon Unfolding," 2001, Visualization, VIS '01. Proceedings, pp. 411-418.

Australian Patent Office, Examiner's First Report, Sep. 18, 2007.

\* cited by examiner

| This Screening Exam Represents A New and Unique Concept In Personal Awareness |
|---|
| CT (Computerized Tomography) "Virtual Colonoscopy" Exam Results  Pg. 1 of 2 |

| Patient: Doe, John | | Referred by: Self Referred |
|---|---|---|
| Pt.#: 00001 | SUMMARY | Date: 9/27/02 |
| 1. Polyp #1 in the sigmoid colon measures 7mm; DFR (Distance From Rectum) is 35cm.<br>2. Polyp #2 is near the splenic flexure and measures 8x10mm; DFR is 60 cm.<br>3. Polyp #3 in the transverse colon measures 8x14mm; DFR 85cm.<br>4. Polyp #4 & #5 are in the ascending colon, measuring 11x26mm and 4x8mm respectively, DFR for both is 115cm.<br>5. RECOMMENDATION: fiberoptic colonoscopy & resection of these lesions. | | |

INDICATIONS: Evaluate for possible colonic mass or resectable intraluminal polyp (>6mm).

EXAM: A CT exam of the abdomen and pelvis was performed in the prone and supine positions following insufflation of the colon with room air according to the virtual Colonoscopy scanning protocol. This exam is intended only for screening purposes and a clinical correlation discussion of findings with a personal physician is absolutely necessary.

FINDINGS/COMMENT:

| | | RECTUM | Key Images |
|---|---|---|---|
| #1 | Prep/Inflation<br>FINDINGS | The lumen is clear of fluid and/or retained fecal material.<br>The rectum/ampulla shows no evidence for polyp or mass. | |
| | | Sigmoid Colon | |
| #2 | Prep/Inflation<br>FINDINGS | The lumen is clear of fluid and/or retained fecal material.<br>a 7mm diameter polyp is identified approx. 35cm from the rectum. | Ax. #151 |
| | | Descending (Left) Colon & Splenic Flexure | |
| #3 | Prep/Inflation<br>FINDINGS | The lumen is clear of fluid and/or retained fecal material.<br>An 8mm x 10mm polyp is identified near the splenic flexure approx. 60 cm. from rectum | Ax. #63 |
| | | Transverse Colon & Hepatic Flexure | |
| #4 | Prep/Inflation<br>FINDINGS | The lumen is clear of fluid and/or retained fecal material.<br>At midtransverse colon there is an 8x14mm pedunculated polyp approx. 85 cm. from rectum. | Ax. #40 |
| | | Ascending (Right) Colon | |
| #5 | Prep/Inflation<br>FINDINGS | The lumen is clear of fluid and/or retained fecal material.<br>Two polyps are identified. Both are approx. 115 cm. from rectum. The larger measures 11x26mm and appears somewhat flat. The smaller (on opposite wall, partially hidden by a haustral fold) measures approx. 4x8mm. | Ax. #50 |
| | | Cecum & Iliocecal Value | |
| #6 | Prep/Inflation<br>FINDINGS | The lumen is clear of fluid and/or retained fecal material.<br>Cecum is unremarkable. Iliocecal value has a normal appearance | |

You undertook this screening exam to assess your major chest, abdominal and pelvic organs for purposes of excluding obvious structural changes that you should know about. This screening exam DOES NOT and CANNOT evaluate the function of your different organs. We urge you to share this report and the accompanying self launching CD-ROM (containing your images) with your personal physician so that together you may weigh these screening results and decide if any lifestyle or dietary changes....plus additional diagnostic imaging or specialized functional organ specific tests are warranted.

FIG. 15

SYSTEM AND METHOD FOR ANALYZING AND DISPLAYING COMPUTED TOMOGRAPHY DATA

CROSS-REFERENCE TO RELATED APPLICATION

This application claims the benefit of priority to U.S. Provisional Application No. 60/364,269, filed Mar. 14, 2002 and U.S. Provisional Application No. 60/429,827, filed Nov. 27, 2002, the subject matter of each being incorporated herein in its entirety.

BACKGROUND OF THE INVENTION

1. Field of the Invention

The present invention generally relates to analysis and display of data acquired using computed tomography representing various organs of the human body. More specifically, the present invention relates to a computerized system for analyzing data acquired from tubular structures of the body, for example, the colon or gastro-intestinal tract, and displaying that data in a manner providing for rapid evaluation of the tissue structures of tubular structure and the accurate determination of any abnormalities present.

2. Description of Related Art

In industrialized nations, colorectal cancer is the second leading cause of deaths from malignancy. In the United States, almost 150,000 people are determined to have colon cancer annually. Unfortunately, colon cancer also causes approximately 60,000 deaths annually, with only lung cancer causing more deaths among the population of America. What makes these statistics truly unfortunate is that colon cancers are perhaps one of the most preventable of cancers because they usually begin as benign polyps which grow slowly for five to ten years before becoming cancerous. If these polyps are detected and removed, the risk of developing colon cancer is greatly reduced.

Regrettably, widespread colorectal screening and preventive efforts are hampered by several practical impediments, including limited resources, methodologic inadequacies, and poor patient acceptance leading to poor compliance. In addition, a fecal occult blood test (FOBT) fails to detect the majority of cancers and pre-cancerous polyps. Since sigmoidoscopy only examines a portion of the colon, it also misses many polyps. The accuracy of barium enema varies among centers and is therefore not always reliable.

Therefore, there is a need for a new test which can be used to screen for pre-cancerous colon polyps, as well as other abnormalities, such as the thickening of the colorectal wall caused by tumors that might otherwise not be found. Like all screening tests, this new test must be relatively inexpensive, minimally invasive, and highly specific.

A technique using helical (also known as spiral) computed tomography (CT) to create computer simulated intraluminal flights through the colon was proposed as a novel approach for detecting colorectal neoplasms by Vining D J, Shifrin R Y, Grishaw E K, Liu K, Gelfand D W, Virtual colonoscopy (Abst), Radiology Scientific Prgm 1994; 193(P):446. This technique was first described by Vining et al. in an earlier abstract by Vining D J, Gelfand D W, Noninvasive colonoscopy using helical CT scanning, 3D reconstruction, and virtual reality (Abst), SGR Scientific Program, 1994. This technique, referred to as "virtual colonoscopy", requires a cleansed colon insufflated with air, a helical CT scan of approximately 30-60 seconds, and specialized three-dimensional (3D) imaging software to extract and display the mucosal surface. The resulting endoluminal images generated from the CT scan data are displayed to a medical practitioner for diagnostic purposes.

The technique of reformatting 2D cross sections perpendicular to the colon midline is also described in U.S. Pat. No. 5,458,111, issued Oct. 17, 1995 to Coin. However, direct interpretation of the cross-sectional images is difficult because a scan of the colon consists of several hundred axial tomograms. Without advanced image manipulation tools, interpretation of the colon's complex three-dimensional shape from these cross sections alone is very difficult for a medical practitioner.

One approach to improve accuracy involves production of reformatted 2D images at cross sections and orthogonal angles to the colon midline. These reformatted 2D images can provide complimentary diagnostic information when viewed with corresponding intraluminal 3D images. Exam efficiency can be improved with innovative 3D rendering techniques that allow fast, interactive evaluation on low priced computer hardware.

While these techniques have advanced the art of using CT scanning in assisting the diagnosis of colorectal cancers, among other diseases, the prior techniques typically required massive computing capacity and specialized work stations. Moreover, the prior techniques have also been limited to providing views of the colorectal pathway that may occlude the presence of polyps, and which do not provide any information regarding the subsurface morphology of the colorectal pathway, or other tubular structure being analyzed. Typically, the only views provided to the physician or technician viewing the data display are two and three-dimensional endoluminal, coronal, sagittal and axial views of the tubular structure being evaluated.

Generally, a CT scanner and computer workstation are used to image tubular structures of the human body, such as the digestive tract of a living person. The CT scanner is used to generate cross-sectional axial images of a human colon which are then transferred to the computer workstation. A colon midline is defined which follows the colon lumen. The computer workstation supports colon midline definition by generating and displaying reformatted cross-sectional images, volume rendered scouts, and interluminal views. Semi-automatic midline defining tools may also be included. After the midline is defined, a montage of images is displayed for diagnostic purposes. The images include axial sections, transluminal cross section, and intraluminal volume rendered images.

Semiautomatic methods are used to delineate the three-dimensional shape of the colon by identifying its approximate midline. This is supported by the display of coronal, sagittal, and axial views as well as an off-axis plane orthogonal to the midline. Straightened curved sections along the midline and a rendered view from the end of the midline may also be displayed. Editing the midline in any of these views will typically cause the other views to update accordingly. After the midline of the colon is traced, data are extracted so the colon can be examined efficiently.

In general practice using the equipment described above, a medical practitioner, such as a radiologist, examines a tubular structure of a patient, such as the patient's colon, by moving a virtual view point along the delineated midline. Three-dimensional orthogonal off-axis cross sections, volume rendered extra-luminal scouts or the original axial 2D images, and a high resolution perspective rendering of the colon's inner surface may be displayed so that the practitioner can observe the structures of the tissues of tubular structure being analyzed. The perspective views can typically be re-oriented in any direction. A rotatable longitudinal sectioning along the colon's midline may also displayed. This view, which may be advanced along the entire length of the colon, enhances both navigation of the path forward or backward along the 3D images and interpretation of the 3D images.

Experience has shown that the simultaneous display of cross-sectional and rendered views enhances diagnostic interpretation of the CT data more than either cross-sectional or intra-luminal views alone. Volume rendering of the CT data is performed by custom algorithms that use pre-computation of texture and other techniques to achieve interactive performance on moderately priced workstations.

Commonly, at least two views of the three-dimensional images generated as described above are displayed to the practitioner. The first view is typically a forward intra-luminal view which encompasses a view of the colon from the view point looking away from a terminating location of the colon, such as the anal verge. The second view may be a backward intra-luminal view which encompasses a view of the colon from the view point looking toward a terminating location of the colon, such as the anal verge. Displaying both views makes it less likely that a feature of interest will be obscured due to the topology of the colon.

By pointing the cursor on the image and simultaneously pressing a key or otherwise issuing an appropriate instruction to the computer work station, a practitioner can move the view point off the previously defined midline, and all images, including 2D reformatted images, 3D intra-luminal images, and the 2D axial image may be updated to views corresponding to the designated position. The practitioner can randomly move the view point by using the pointing device, or return to the nearest point on the predetermined midline.

To assist in diagnosis, an unfolded or opened view of the colon may also be displayed to the observer. The opened view of the colon corresponds to a view of the entire colon as if it had been physically divided and opened for inspection, just like cutting a garden hose in half along its longitudinal axis, maintaining the curvature of the colon. However, this "unfolding" technique only allows a view of the internal structure of the tubular structure or colon, and does not provide a truly "flattened" view of the internal wall of the colon, wherein the inherent curvature of the colon is "flattened", thus allowing structures that protrude from the inner wall of the colon, such as Haustral ridges, to hide structures such as small polyps or other anomalies from the practitioners view.

Moreover, none of the systems, methods or techniques currently available are believed to be able to provide an assessment of the wall of the tubular structure. For example, some colorectal cancers do not grow out of polyps, but instead manifest themselves within the walls of the colon. Such cancers cannot be observed using the means described above, since none of those methods allow for an analysis of the wall thickness or density of the tubular structure.

What has been needed, and heretofore unavailable, are techniques which provide efficient and accurate presentation of CT data that provided a flattened view of a tubular structure that prevents structures within the tubular structure from obscuring the view of anomalies such as polyps in a colon. Moreover, such techniques should be able to run efficiently and quickly on commonly available computer platforms, such as on computers manufactured by Apple or on IBM clones. Additionally, such a system should be able to also analyze anomalies present in the wall of the tubular structure, such as variations in wall thickness or density that may indicate the presence of tumorous growths or other disease. The present invention satisfies these and other needs.

SUMMARY OF THE INVENTION

In its broadest aspect, the present invention is embodied in a system and method of rendering three-dimensional images that provide a user with views of data generated by a scanner of selected portions of the human body that are designed to assist the user, or another person, such as a surgeon or physician, in diagnosing disease conditions and in prescribing treatment for those conditions. Also disclosed is a system and method for further processing three-dimensional volume data using appropriate pattern recognition and analysis software to identify abnormalities in imaged bodily structures, particularly in tubular structures, such as the colon, of the body.

In one aspect, the present invention is embodied in a method of imaging a tubular body structure having a lumen defined by a wall, comprising the steps of providing a data set containing data representing a plurality of cross-sectional images of a tubular structure of the body taken along a longitudinal axis of the tubular body, processing the data set to reconstruct a three-dimensional image of the tubular body, identifying a central pathway through a lumen of the three-dimensional image, selecting a starting point along the central pathway, processing the data beginning at the starting point and continuing along the longitudinal length of the three-dimensional image of the colon and rendering a flattened view of the three-dimensional image, storing data representing the flattened view in an image buffer, and displaying the flattened view of the image.

In another aspect, the present invention is embodied in a method that further includes selecting a point along the central pathway, processing the data at the selected point and rendering an image of a cross-section of the wall of the tubular structure at the selected point, and displaying the image of the cross-section of the wall of the tubular structure.

In yet another aspect of the invention, the invention includes processing the data and rendering the flattened image, projecting a ray from the starting point to the wall, the direction of the ray corresponding to an angle of view, and adding a voxel value to an image buffer. In one alternative, the method may also include shifting the angle of view by one degree, and projecting another ray from the starting point to the wall, the direction of the ray corresponding to the shifted angle of view if the angle of view has not been shifted a total of 360 degrees from the initial starting point. In still another alternative, the method also includes advancing the starting point along the longitudinal axis of the lumen by a selected value if the angle of view has been shifted a total of 360 degrees from the initial starting point, and repeating the steps of projecting the ray and storing voxel values in an image buffer until the entire length of the lumen has been processed.

In yet another embodiment, the present invention includes a method for generating a view of the interior of a wall of tubular structure of a body including tissue adjacent the exterior of the wall, comprising:

(a) providing a data set containing data representing a three-dimensional volume representing a tubular structure of the body taken along a longitudinal axis of the tubular body, the tubular body having a lumen defined by a wall;

(b) selecting a starting point along a central pathway disposed along the longitudinal axis of the tubular body;

(c) projecting a ray towards the wall a selected distance by stepping towards the wall along the ray from the starting point;

(d) calculating a voxel value at the location of each step of the ray;

(e) adding the voxel value to an image buffer;

(f) incrementing the angular projection of the ray one degree;

(g) determining if the angular projection of the ray has been incremented 360 degrees since the starting point was selected;

(h) projecting a ray having the incremented angulation toward the wall;

(i) repeating steps (d) through (h) until the angular projection of the ray has been incremented 360 degrees; and (j) displaying a subsurface volume image.

In another embodiment, the present invention includes comparing a three-dimensional volume data set to a library of geometrical patterns representative of predetermined abnormalities, and identifying a structure contained in the three-dimensional volume data set as abnormal if the structure is determined to match at least one of the library of geometrical patterns within a predetermined tolerance. In an alternative embodiment, the present invention includes further processing the identified abnormal structure to determine if the identified structure is not abnormal.

In still another aspect, the present invention is embodied in a computer having a processor, a program memory and a semi-permanent storage memory. The processor is programmed by a software program designed to receive data sets generated by a scanner, process the data in the data sets in its memory to render three-dimensional views of the scanned data, and also render flattened views of the scanned data. Alternatively, the processor processes the scanned data to render subsurface views of a structure of interest Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 15 is a graphical representation of another embodiment of a report generated using the system and methods of the present invention that is coordinated with the embodiment of FIG. 14.

DETAILED DESCRIPTION OF THE PREFERRED EMBODIMENTS

Figure 1:
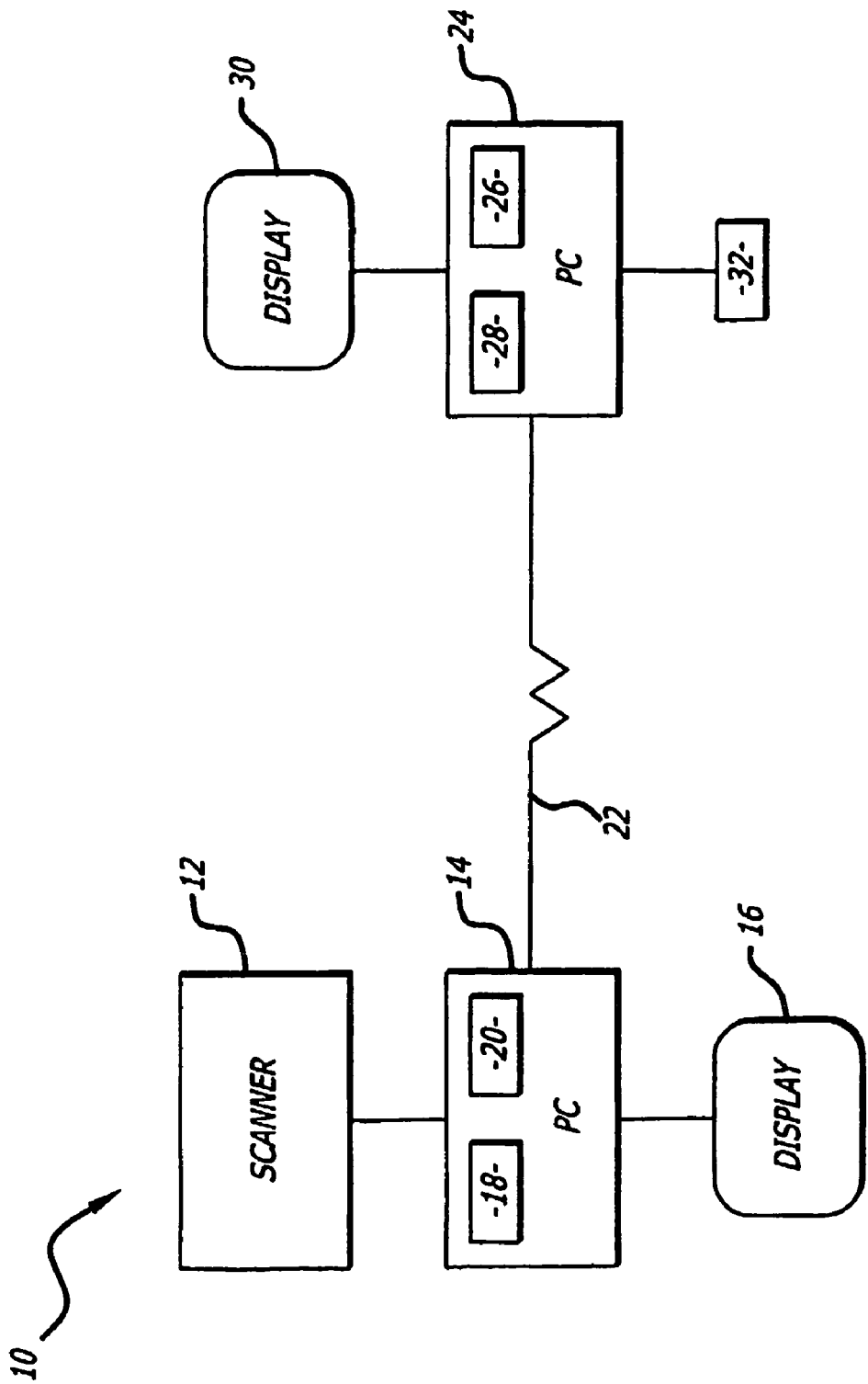
FIG. 1 is a graphical representation of a system for taking CT scans of a patient, including communication means for transmitting the CT scan data to a remote computer for processing and display in accordance with embodiments of the present invention.

The present invention generally relates to a method and system for generating and displaying interactive two- and three-dimensional figures representative of structures of the human body. The three-dimensional structures are in the general form of selected regions of the body and, in particular, body organs with hollow lumens such as colons, tracheobronchial airways, blood vessels, and the like. In accordance with the method and system of the present invention, interactive, three-dimensional renderings of a selected body organ are generated from a series of acquired two-dimensional images generated from data acquired by a computerized tomographic scanner, or CAT scan. Recent advances in CAT scanning technology, notably the advent of use of helical or spiral CAT scanners, have revolutionized scanning of human body structures because they allow the collection of a vast amount of data in a relatively short period of time. For example, an entire colorectal scan may be accomplished in the time a patient can hold his or her breath However, as will become clear to those skilled in the art, any type of digital image that can be derived from a data set produced by a scanner, such as those produced by CAT scanners, magnetic resonance (MRI), photon emission tomography scanners (PET), ultrasound equipment and the like may be processed using the system and method of the present invention.

Typically, a patient is located within the scanner and the a scan is made of a desired portion of the patient's body. The data set representative of the scan of the patient is extracted and stored with appropriate identifying information. The data set may then be transferred to a computer work station for analysis. As is known in the art, the scan data may be compressed so that it can be transmitted to an analysis site by a variety of means. For example, the present invention is particularly suited for use on computer work stations based upon a personal computer, such as a Macintosh computer or IBM clone computer that have appropriate amounts of working memory, processing power and hard drive storage capacity. The inventors have operated software embodying the present invention of a Macintosh G4, sold by Apple Computer, Inc., as well as other computers.

Because the system and method of the present invention does not require a specialized work station, such as previous methods used to reduce CT scan data and generate three-dimensional images, CT scan data may be sent over the internet, local area network or telephone lines using suitable communications devices and techniques well known in the art to computers and workstations located remotely from the scanner location operating under the control of software incorporating aspects of the present invention for further processing and analysis.

A patient is initially prepared for imaging by cleansing the patient's colon. The purpose of the cleansing procedure is to eliminate feces from the colon. Optimally, an absolutely clean colon is desired prior to CT scanning, as any retained feces or fluid can simulate or mask small polyps.

Once the colon has been cleansed, the colon is insufflated with gas to distend the colon. Distending the colon assures that the interior surface of the colon will be clearly visible in the final image display. A rectal catheter, i.e., a standard barium enema catheter (0.5 inch (1.27 cm)) diameter is inserted and gas is introduced into the colon. The colon is filled to a predetermined pressure or volume by introducing the gas either as discrete puffs or at a constant flow rate. Although air can be used, $CO_2$ may be preferred since $CO_2$ passes through the colonic mucosa into the bloodstream and is subsequently exhaled, thereby decreasing the amount of bloating and cramping experienced by a patient after the examination. Unlike conventional colonoscopy, there is no need to sedate the patient for this procedure.

After insufflation, the colon is then scanned by, for example, a helical CT scanner to produce a series of two-dimensional images of the colon. The picture elements, or pixels, in the images represent at least one physical property associated with the colon. The physical property, for example, may be the x-ray attenuation of the colon wall or of the air column within the colon. The images are generally taken at regularly spaced locations throughout the abdominal region of the patient. The smaller the spacing between successive images, the better the resolution in the final displayed imagery. Preferably, the spacing between successive images is approximately 1 mm to produce isotropic voxels since the X and Y dimensions of each voxel are each approximately 1 mm.

Immediately after inflating the colon, the abdomen is scanned, for example, with a GE HiSpeed Advantage Helical CT Scanner, during a single breath-hold acquisition which is completed in about 30-50 seconds. The scanning parameters may consist, for example, of a 0.20 inch (5 mm) x-ray beam collimation, 0.4 inch/sec (10 mm/sec) table speed to provide 2:1 pitch, and a 0.04 inch (1 mm) image reconstruction interval. The x-ray beam collimation is the width of the x-ray beam which thereby establishes the CT slice thickness and Z-axis spatial resolution. The pitch is the CT table speed divided by the collimation. The image reconstruction interval reflects the interval at which two-dimensional images are reconstructed. Using an x-ray beam collimation of 5 mm and a selected reconstruction interval of 1 mm, images reflecting a 5 mm CT slice thickness are generated at 1 mm intervals. Consequently, there is an overlap of 4 mm between successive 5 mm thick images at a 1 mm reconstruction interval.

A 50 second scan at a table speed of 10 mm per second in a Z-axis direction creates a volume of data having a Z-axis length of 500 mm. Using a 1 mm reconstruction interval over the length of the Z-axis of the volume of data produces 500 images with each image representing a 5 mm thick section along the Z-axis. Typically, the scan is done twice, once with the patient in a prone position, and once with a patient in a supine position, thus generating approximately 1000 images. Newer multi-slice CT systems, including those having 4 and 16 channels of data acquisition bandwidth, can obtain 5 mm thick slices every 2 mm in about 30-40 seconds, yielding data sets having 200-250 images. Scanning 2.5 mm thick slices every 1.0 mm increases that number to 400-500 images per data set. After completion of the CT scan, the rectal catheter is removed, the gas is expelled, and the patient is discharged.

FIG. 1 generally depicts a system that may be used to render images in accordance with the principals of the present invention. System 10 includes a scanner 12 that is connected to a computer 14. Computer 14 is used to control the operation of the scanner 12, and is also used to acquire data generated by the scanner 12. The computer 14 may be any computer having sufficient computational power, storage and memory so that it is capable of running customized software for controlling the scanner and acquiring and storing the data generated by the scanner during a scan of a patient's body, or selected portion of a patient's body. The computer 14 also includes, besides a processor or microprocessor capable of being programmed using custom software, a memory 18 which may be random access memory or read only memory, and suitable storage media 20, which may include, for example, a hard drive, a CD or DVD drive, or other storage media suitable for storing the data generated by the scanner. A display 16 is connected to computer 14 to allow an operator to view displays of data and operating parameters for the scanner, as well as images rendered from the data generated by the scanner. Additionally, although not shown, computer 14 will also be operably connected to a device that allows input of commands by the user of the scanner. Such input devices include a mouse or other pointing device, a key board, bar code scanner or other device.

The computer 14 may also be operably connected to a modem or other communication device that allows provides connectivity to a communication means 22, such as a telephone line, cable, DSL connection, local area network, the Internet, or a wireless network. This allows the computer 14 to communicate with other suitably programmed computer systems or workstations 24, providing for the transmission of data generated by the scanner to the other computer systems or workstations 24.

Computer or workstation 24 is similarly equipped to communicate via communications means 22 with computer 14, providing for communication of analysis and reports generated on the computer 24 to a user of computer 14. Computer 24 also includes a processor or microprocess, memory 26 and storage media 26. Additionally, a mouse or other pointing device 32 may also be connected, either through a wired or wireless connection, to allow input of commands to the software program running on computer 24 to control the operation of aspects of the software program. The processor of computer 24 will typically be programmed with custom software incorporating the methods of the present invention to provide various views of the data generated by the scan which are displayed on the display 30. While the methods of the present invention will be described below as if the software operating in accordance with those methods is controlling computer 24, it will be understood by those skilled in the art that the same software may operate and control computer 14, providing a user of computer 14 with the same analysis, views and reports that are generated by computer 24 without the need to transmit data generated during the scan of a patient to a remote location.

Figure 2:
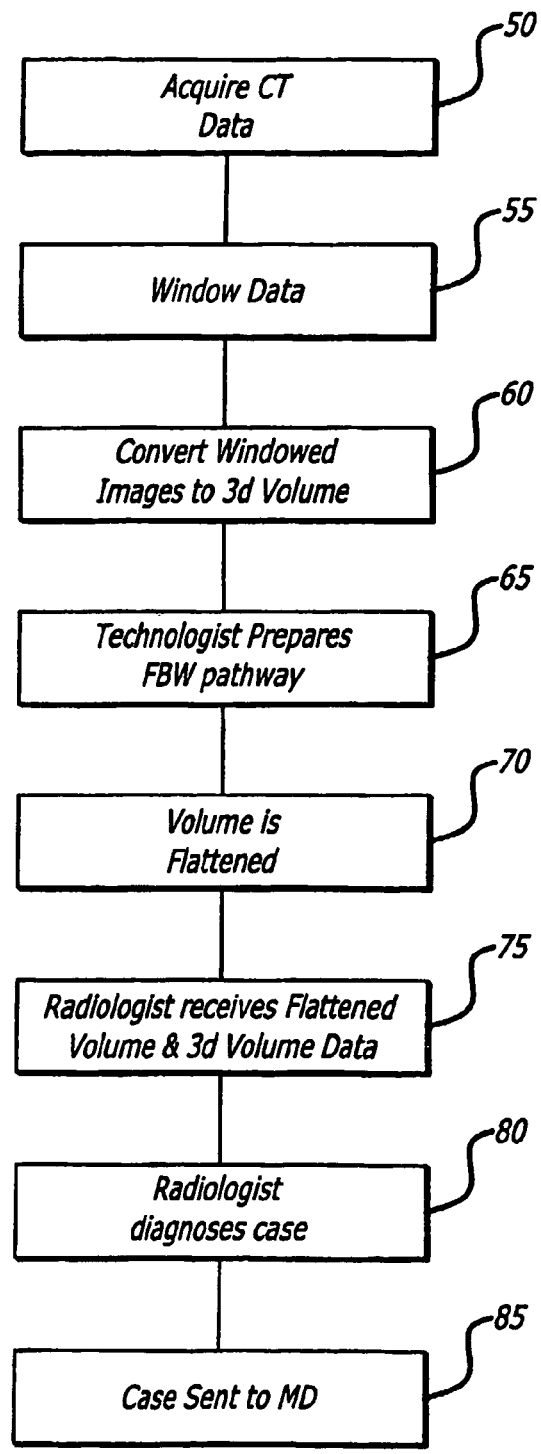
FIG. 2 is a block diagram illustrating a generalized process using embodiments of the present invention for diagnosis.

Referring now to FIG. 2, a generalized flow-chart illustrating the flow of data through a system operating software programmed to carry out the methods of the present invention is depicted. A database containing CT scan data is acquired, either by receiving the database over a wire based or wireless communication system. Alternatively, the database may be manually provided to the system, such as through the use of a portably hard drive, Zip disk, CD or DVD or other portable storage media having sufficient capacity.

The scan data typically consists of a series of two-dimensional images that represent slices taken through the structure that was the subject of the scan. The two-dimensional images are converted or transformed into a three-dimensional image. The two-dimensional images may be typically obtained from a helical CT scanner operated by a computer console. For example, the scanner may be a General Electric HiSpeed Advantage Helical CT Scanner connected with an optional General Electric Independent computer console or physician's console. The computer console may, however, be an integral part of the helical CT scanner instead of a separate independent console. The two-dimensional images can also be obtained from ultrasound, positron emission tomography, emission computed tomography, and magnetic resonance imaging. The physical property measured is directly associated with the scanning technique used to produce the two-dimensional images. For CT images the physical property measured is typically x-ray attenuation, while for magnetic resonance images (MRI) the physical property measured is generally related to various properties such as proton density.

Each of the individual two-dimensional images defines a two-dimensional (X-Y) matrix of picture elements, or pixels, with each pixel representing a predetermined physical property associated with the three-dimensional structure or organ at a particular location within the three-dimensional structure. Successive two-dimensional images are spaced in a third-dimensional direction (Z) throughout the three-dimensional structure.

Typically, the analysis continues by stacking the series of two-dimensional images to form a three-dimensional volume 13, thereby defining a three-dimensional matrix (X, Y and Z axes) that represents at least one physical property associated with the three-dimensional structure at coordinates positioned throughout the three-dimensional volume. The three-dimensional matrix is composed of three-dimensional volume elements, or voxels, which are analogous to two-dimensional pixels. From the three-dimensional volume, a targeted volume may be selected for three-dimensional rendering. For example, the targeted volume may include a selected organ or region of interest that is to be isolated from the original three-dimensional volume. The targeted volume may include an entire organ or, alternatively, may include an air column or volume confined within an organ or a lumen of the organ.

A dataset representing the original three-dimensional volume may be optionally subjected to a dataset reduction process to decrease image or spatial resolution or to divide the original volume into smaller subvolumes of data prior to isolating the targeted volume. Dataset reduction and/or subvolume selection are only necessary if the capabilities of the graphics computer are inadequate to process the full three-dimensional volume for effective or efficient three-dimensional rendering. In order to obtain three-dimensional constructions in real time, it may be necessary to reduce the size of the dataset representing the three-dimensional volume of images. For example, the dataset of the original three-dimensional volume may need to be reduced from an original size of 100-250 Megabytes to a reduced size of about 5-10 Megabytes. However, the amount of reduction, if any, may vary depending upon the size of the original dataset and the processing speed and capability of the computer used for three-dimensional rendering.

Following dataset reduction, the three-dimensional image of the organ or region of interest is segmented or isolated from the volume of data. A range of tissue values, which depends on the physical property measured, for example, x-ray attenuation, may be selected to designate the organ or region of interest. The organ or region of interest is then isolated from the volume of data. The region of interest may, for example, be the air column comprising the colon or tracheobronchial airways, or some other body part having a lumen filled with a homogeneous substance such as air, blood, urine, contrast agent and the like. Alternatively, the region of interest may be a section of bone.

The segmentation process may be effected, for example, by designating a range of physical property values bounded by threshold limits that function to designate the organ of interest. For the selected volume or subvolume, voxels falling within a selected thresholding range are assigned a single value, for example, 255 to provide a white color, whereas voxels falling outside of the selected thresholding range are assigned a different single value, for example, 0 to provide a black color. Accordingly, the selected volume is thresholded by comparing each voxel in the selected volume to the threshold limits and by assigning the appropriate color value 0 or 255 to each such voxel depending on whether each such voxel falls inside or outside the threshold range defined by the threshold limits. By thresholding the selected volume, the target volume is formed having equal voxel values. More specifically, a target organ is produced having a white color while all volumes outside the threshold limits are produced having a black color. With the exception of various artifacts, which can be eliminated using image-processing techniques, only the thresholded target organ is colored white and everything else is colored black.

Returning again to FIG. 2, once the CT data is acquired in box 50, the data may be input into a sub-program that segments the data and allows a radiologist or technician to annotate the data set and prepare an overall report, such as is represented by box 55. This step is optional, and may be omitted without departing from the principals of the present invention.

Whether or not the data is processed by the method of box 55, the scan data is modified and output as two-dimensional images, and are stored in a predetermined memory location, such as a folder identified with pertinent patient identifying information, in a suitable file format such as, for example, a "pict" file. Those skilled in the art will understand that other file formats may be used, particularly formats that are capable of storing the image data while maintaining the full bit depth of the original axial images while avoiding the necessity of clipping or compressing the images in a lossy manner.

Once the data is stored in a series of two-dimensional images, the data may be imported into a sub-program that allows the data to be manipulated as described above and rendered into three-dimensional images, as in box 60. One program that can be used has been developed by the inventors and titled VISUALIZE, although any rendering program that can transform or convert two-dimensional images into three-dimensional images having appropriate resolution may be used. For example, the rendering process can be accomplished using a general purpose volume visualization program, such as IRIS Explorer™.

Images of three-dimensional objects, such as the tubular structure of a colon, are projected to two-dimensional screen coordinates for displaying the data to an observer using ray-tracing techniques. Imaginary rays sent from a user's viewpoint pass through a viewing plane, referenced to the user's monitor screen, and into the object. If a ray intersects an object, the corresponding viewing plane pixel is painted with a color different from the background color. If no intersection is found, the pixel is painted as background. The criteria used to stop a ray determines what value is projected onto the viewing plane pixel. This process is different from surface rendering, which typically uses polygon rendering to generate an image; in contrast, volume rendering projects a weighted average of all voxels along a ray to generate an image.

The three-dimensional images may now be displayed on a monitor in a form that provides the user with the ability to "fly" through the tubular structure, for example, the colon. In order to facilitate the fly through, and also to allow for more advanced analysis and display of the three-dimensional images, a central pathway through the colon is determined in box 65. This step will be discussed in more detail below.

Once the fly by wire pathway is determined in box 65, the data is further processed in box 70 to provide a flattened view of the colon. The flattened view of the colon provides a view that may be likened to carefully slitting the colon and spreading the colon on a board so that the curvature of the colonic wall no longer obscures structures such as polyps, that may otherwise be hidden when viewed using more traditional multi-planar views. Additionally, further processing of the data may be performed to generate a subsurface view of the wall of the colon, synchronized with the flattened view, to assist in diagnosis of colonic wall abnormalities, such as flat tumors or wall constrictions, that might otherwise not be apparent when viewing only the flattened image.

Once all desired image processing is completed, data sets containing the processed image data are stored. It will be understood that these data sets contain data arranged in a form that allows a user to view images in the data set as if the data set were a movie. This arrangement allows a physician evaluation the scan data to fly through the colon in any direction, and to jump to a selected portion of the colon where abnormalities have been detected and marked for further analysis.

In one embodiment of the present invention, the data sets may be transmitted to a radiologist who receives the flattened volume view, 3D volume and subsurface view data for analysis, as indicated in box 75. The radiologist then views the data, and renders his diagnosis of the case in box 80. The diagnosis report is then sent to a surgeon and/or the patient's physician in box 85.

Figure 3:
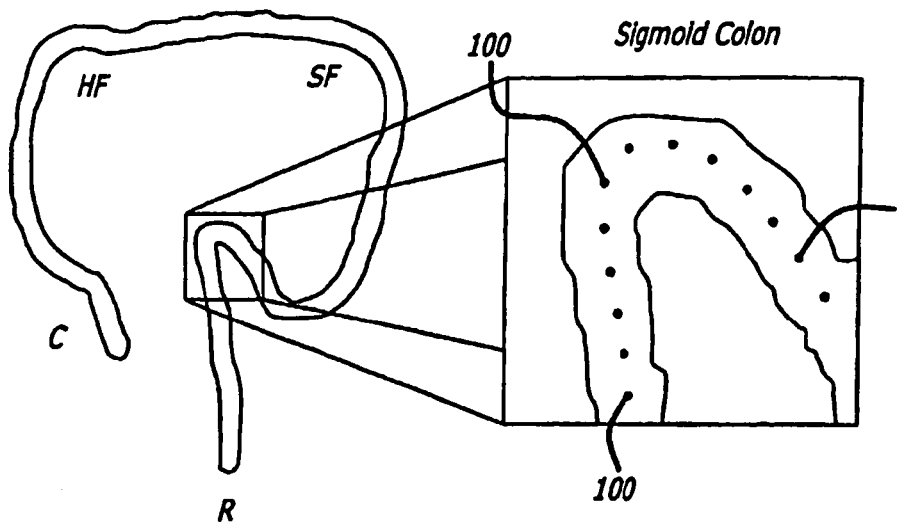
FIG. 3 is a view of a two-dimensional image of a patient's colon showing identification of luminal center points of a fly by wire pathway.

Various aspects of the system generally described with reference to FIG. 2 will now be described with more specificity. Referring now to FIG. 3, the determination of a central pathway in the colon will now be described. As shown in the figure, a section of the colon, here, the sigmoid colon, has been identified as an area of interest. Center points 100 along the lumen of the colon are identified, using either specialized software, or manually by an appropriately trained technician. While automated center "fly by wire" pathway generation may be used, often manual determination is advantageous to ensure that an accurate pathway through what is sometimes a tortuous, constricted or collapsed pathway is obtained. As shown in FIG. 3, a series of points have been identified within the central lumen of the colon by a technician. These points are identified by scrolling through the two-dimensional multiplanar representation of the colon and pointing a mouse or other suitable device at a desired location and clicking to mark the point in the data base representative of the desired center point. The software memorizes this location and associates it with other so-determined center points to determine the fly by wire pathway.

The center line of the colon can be determined in one of several ways. For example, in one method of determining the central path through the lumen of the colon, a first point is selected which lies within the lumen of the colon at a desired starting location. The plane through the starting point that has the minimum cross-sectional area is determined and the center of such area is marked. A new point is then selected which lies, for example, 1 cm away from center point in a perpendicular direction relative to the surface area in the plane. A new plane of minimum area that dissects the colon and passes through the new point is determined and the corresponding center of that new area is marked. This iterative process is continued until a central path connecting the center points is determined. As stated previously, this is but one of a variety of methods that may be used to determine the central path through the lumen of the colon, and is not intended to be limiting in any way.

Once the fly by wire pathway has been determined, the data may be processed in real time to provide a movie-like fly through of the entire length of the colon, or selected portion of the colon. Moreover, the system and method of the present invention allows the data display to be halted whenever a user desires with an appropriate mouse click or key board command. This allows the user to halt the fly through if the user observes an area of the colon that requires closer evaluation, such as for the presence of a polyp or tumor. As will be described in more detail below, the location within the colon where an anomaly is identified by the user may be displayed to the user in a variety of ways.

Animation of three-dimensional objects, such as that described above as a "fly through", is achieved by rapidly displaying multiple three-dimensional views of the volume. Surface rendering calculations using presently available computer platforms are fast enough to allow interactive manipulation of the volume. Additionally, the rendering software typically includes modules that provide the ability to enhance an object's features by altering the shade of color of each viewing plane pixel. For example, "shaded surface" images add an illusion of depth by coloring pixels closer to the camera viewpoint with lighter shades. Pixels in a shaded surface image reflect the distance between the anatomical structure and the user's viewpoint. Information on the relative "position" of the user and a virtual light source, along with the information about the rendered structure, are used to appropriately shade the rendered volume to produce a realistic impression of the anatomy.

As described, the rendering or converging step 60 occurs rapidly and interactively, thus giving the user the ability to "fly" through the volume of data. The direction of "flight" is controlled by using the mouse or commands entered through the key board through directional pointing of the cursor, and the speed (both backwards and forwards) may also controlled by pressing buttons on the mouse or key board. The speed of interactive three-dimensional rendering produces a "virtual reality" environment and allows the user to examine the image data in a manner that is analogous to real endoscopy.

The path of each simulated flight, whether relative short, or local, or a long distance flight through out the whole or a major portion of the colon, can be recorded and used in a "playback" mode to retrace the flight path. Individual three-dimensional scenes may also be stored on the computer like photographs. Each simulated "flight" through the colon can be recorded on VHS videotape on a video recorder, or on other suitable storage media, for archival purposes if desired. Additionally, the data may be stored so that it may be transmitted to gastroenterologists and surgeons for further review and analysis.

To achieve an adequate speed of rendering but still preserve the anatomical detail of the original CT data volume, it is possible to navigate or "fly" through reduced three-dimensional imagery built from the reduced dataset volume. When the motion stops, however, the three-dimensional scene may be redisplayed with the highest resolution possible using the original CT image volume.

Additionally, it is useful to display other images, such as axial images and multiplanar orthogonal axial, sagittal and coronal images during the fly through to assist the user in analyzing the morphology of the colon. An example of such a display is depicted in FIG. 4.

Figure 4:
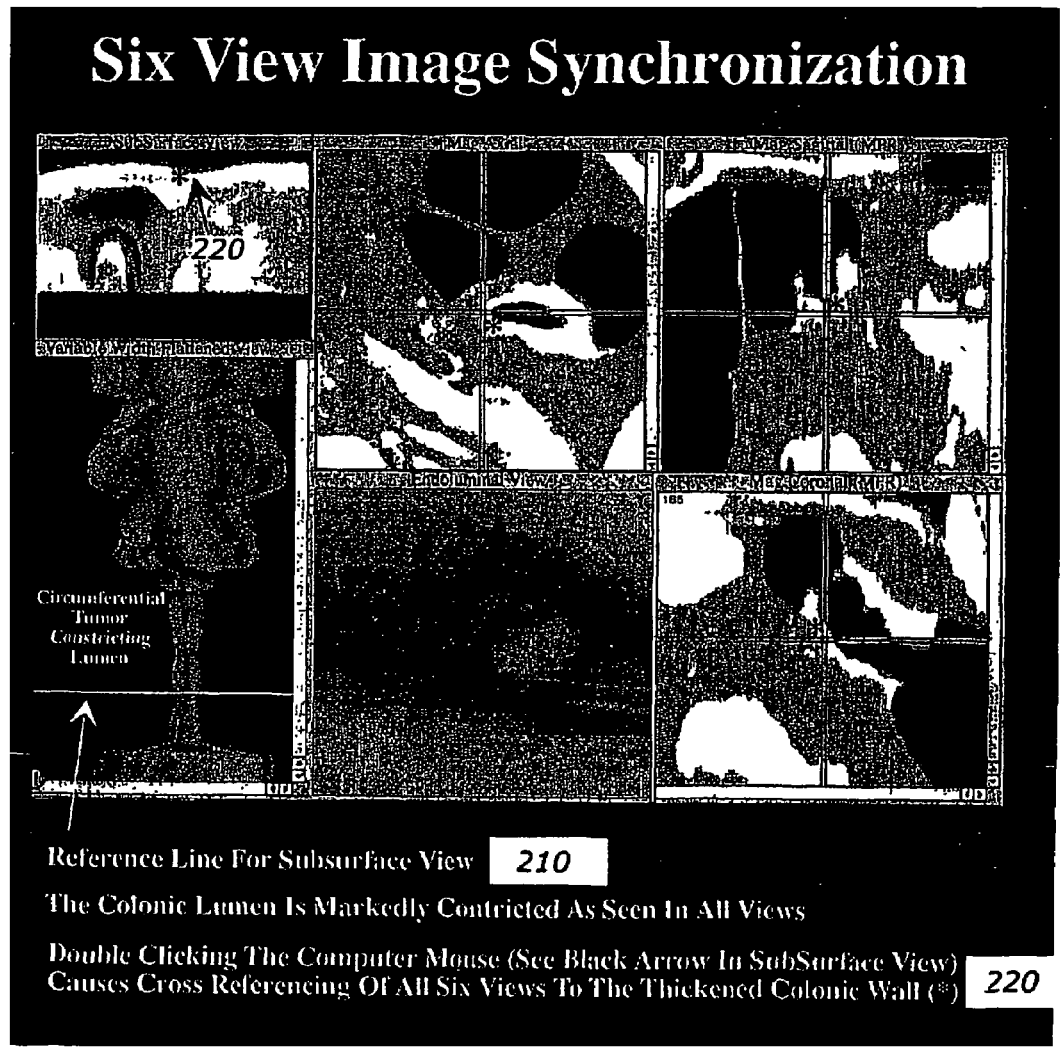
FIG. 4 is a view of a representative display showing various views of a patient's colon derived from CT scan data using the methods of present invention.

FIG. 4 shows six separate synchronized views of the colon that were rendered using the methods of the present invention. As shown, reference line 210 points to a particular location within the colon that has been identified during the fly through as having structure that required further evaluation. In this mode of operation, the user flies through the colon using the mouse to control the speed and direction of flight. By clicking on the reference line, the images may be advanced or backed up, allowing the user to fly both upstream and downstream. As the user flies through the colon, the reference line moves on the image titled "Variable Width Flattened View", to be described in more detail below, indicating the location within the colon of the displayed views. Each of the other views, such as the Mag Axial, Mag Sagittal (MPR), Endoluminal and Mag Coronal (MPR) views are synchronized with the reference line, allowing a practitioner to study an anomalous structure from a variety of view points.

Additionally, the display shown in FIG. 4 includes a Subsurface View, which will be described in more detail below. This view allows a physician or trained technician to also inspect anomalies in the wall of the colon. This ability to synchronously display the wall thickness of the colon allows for diagnoses of tumors and other disease that may not manifest as polyps or other anomalous structures that may be seen on the interior surface of the colon. As shown by the "*" 220 in the Subsurface View, and the cross-hairs in the other views, all of the views have been synchronized to an area of thickened colon wall, providing the user with a variety of views to assess the wall, and to correlate the wall thickness with any other structural abnormalities of the colon.

The subsurface view is capable of being "windowed", that it, the parameters used to generate the view may be altered as desired by the user. For example, the available contrast limits may be adjusted to optimize display of small abnormalities, or the resolution of the view may be adjusted. Alternatively, limits on the degree of parameter adjustment or windowing may be programmed into the software to prevent high contrast, narrow, "lung" setting that are commonly used in two-dimensional axial, sagittal and coronal polyp searches. If the "lung" windows used are too narrow, a user viewing two-dimensional multiplanar views may not observe a constricting tumor if the user fails to adjust the windowing parameters to evaluate the thickness of the wall of the colon.

General System Description

Figure 5:
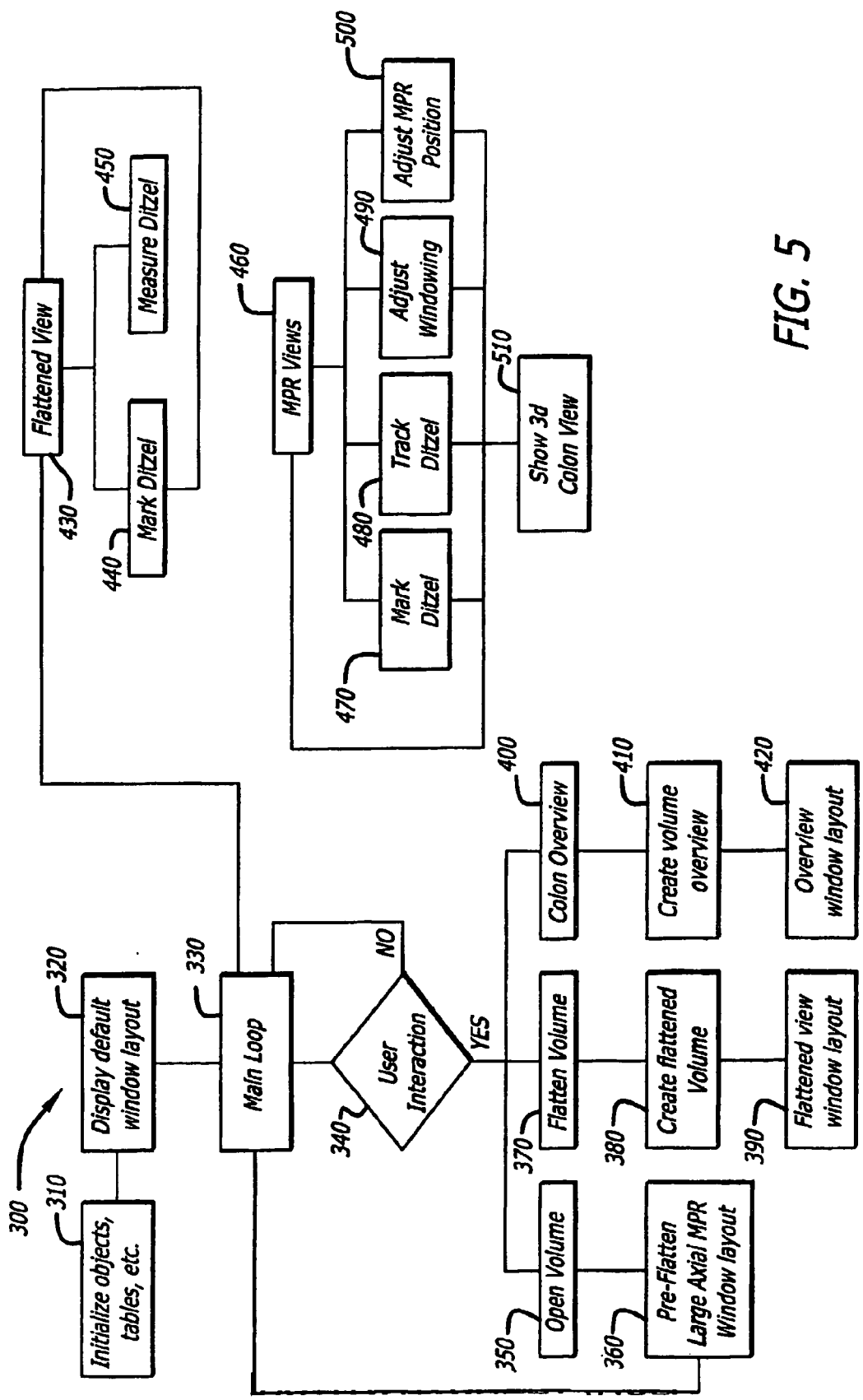
FIG. 5 is a schematic view showing the general processes of a software program incorporating methods of the present invention.

FIG. 5 is a flow chart which sets forth in general the hierarchical structure and flow of information through the system and method of the present invention. System 300 begins, as is typical for software programs, by calling and initializing various variables, objects, look up tables and other user definable sub-processes in box 310. After the initialization is completed in box 310, the monitor displays a default window layout in step 320. Main loop 330 may then be initialized, and awaits user input to determine which portion of the image to be displayed is rendered on the monitor. As previously described, once a user is presented with an overview of the beginning portion of the colon, the user may use a mouse, or keyboard command, or another pointing device, to generate signals that direct the computer upon which the software is operating to scroll through the stacked three-dimensional images that form the three-dimensional volume to be displayed. As the user inputs commands into the computer to scroll through the data, various sub-programs are initiated, such as sub-program 350, which opens the three-dimensional volume and provides a pre-flattened large axial multi-planar window layout in step 360. In one embodiment of the present invention, this step provides rapid rendering of two-dimensional multiplanar images which may be used to by the user to manually designate center points of the luminal image. Alternatively, the data comprising these views may be analyzed using software designed to automatically determine and designate luminal center points, and automatically advance, slice by slice, through the entire length of the colonic image, or a designated portion of the colonic image, to determine the fly by wire pathway through the colon.

Additionally, as indicated by box 370, and as described with reference to the multiple view display depicted in FIG. 4, the software embodying the present invention performs the calculations necessary to flatten the segment of the tubular structure being rendered and creates a flattened volume in box 380, and then displays the flattened view in step 390. While the various views are being calculated, an overview of the colon may also be generated in steps 400 through 420 and displayed along side the various other views.

Once the scrolling or the fly through of the colon is completed, box 430 provides for further analysis of the flattened view to identify abnormalities in the colon. For example, when a user observes an abnormality in a particular flattened section of the colon, that abnormality may be marked as in box 440, and measured as in box 450. Additionally, local voxel density measurements may be made of a suspected abnormality to attempt to distinguish the suspected abnormality from, for example, fecal material or an air filled diverticulum. These measurements may be recorded for further analysis, and the location of the abnormality, established by marking the abnormality in box 440, may also be stored, or provided in a menu of marked abnormalities or provided as a print out for further analysis by a user.

FIG. 5 also depicts the various sub-processes that can be undertaken from the multi-planar (MPR) views that are displayed in FIG. 4. For example, if an abnormality in a particular MPR view is observed, it may be marked as in box 470. Additionally, as the fly through of the colon proceeds, the abnormality may be tracked to determine its extent and general shape, as indicated in box 480. The images provided to the user comprise, in essence, an endoluminal movie created along the fly by wire pathway from one end of the colon, for example, the rectum, to the other end, or cecum, of the colon. The movie may also run in reverse to allow a flight from the cecum to the rectum. In the endoluminal views produced by the present invention, the fly through includes a pointer that can be locked onto the location of a abnormality by the user, and that allows the movie to be played in order to display various aspects of the abnormality, assisting in location, identification, observation and diagnosis of the abnormality.

The various MPR views also provide the user with the ability to alter the windowing of the view, that is, adjusting the size of the window so that abnormalities or features of interest of various size may be included within a single window, in a sort of zoom in or zoom out function, as in box 490. Moreover, the position of the multi-planar view may be adjusted as necessary to ensure that to the extent possible, any abnormalities that might be hidden by structures such as Haustral ridges will be visible, as indicated by box 500. The MPR views may also include the ability to show a 3-D view of the colon, as indicated by box 510, may be windowed for contrast adjustments, and may be used to trigger the fly over local movie, described above, to localize the viewing of selected abnormalities.

Flattening Module

The present invention includes a method for "flattening" the rendered volume representative of a tubular structure. Previous attempts at providing a flattened view have used various methods to display a longitudinal section of the colon, such as would be obtained by slicing though a chord of the tube. The disadvantage of these methods is that the overall view of the colon remained curved, unless such a small chordal diameter for the section was used as to provide no useful data. In contrast, the inventors have developed a method of truly flattening the image of the colon in a manner that may be likened to making a single slice through the wall of the colon and unrolling the tubular structure of the colon until it lies flat. By flattening the colon in this manner, surface abnormalities are highlighted and made visible, even if previously hidden by structures of the colon, such as Haustral ridges.

Figure 6:
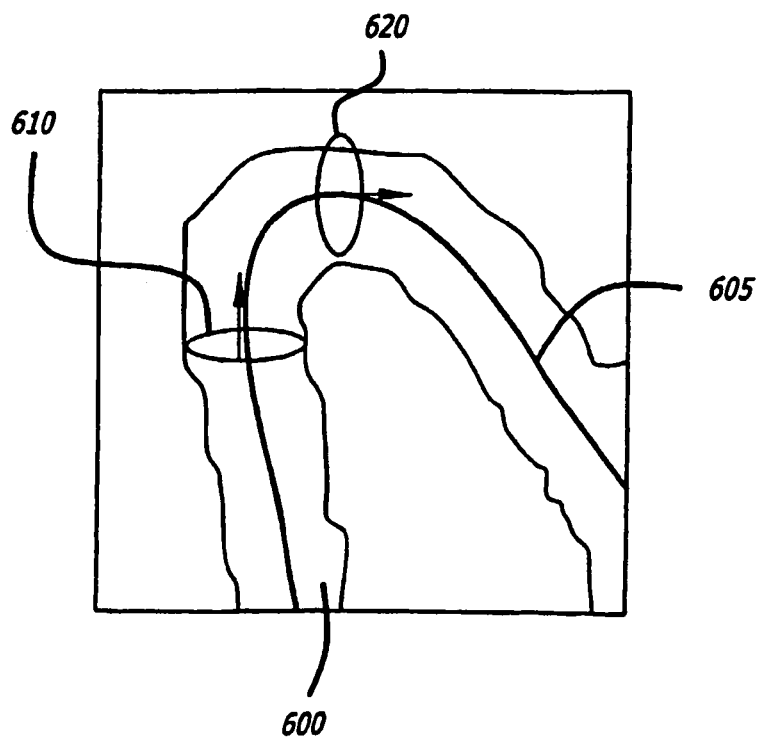
FIG. 6 is a view of a two-dimensional image of a patient's colon rendered in accordance with the methods of the present invention.

FIG. 6 depicts view of a colon 600 showing a fly by wire pathway through the luminal center of the colon 605. Also shown in FIG. 6 are colon segments 610 and 620, which represent thin slices of the colon which may be converted from a three-dimensional tubular structure into a flattened view in accordance with principles of the present invention.

Figure 7:
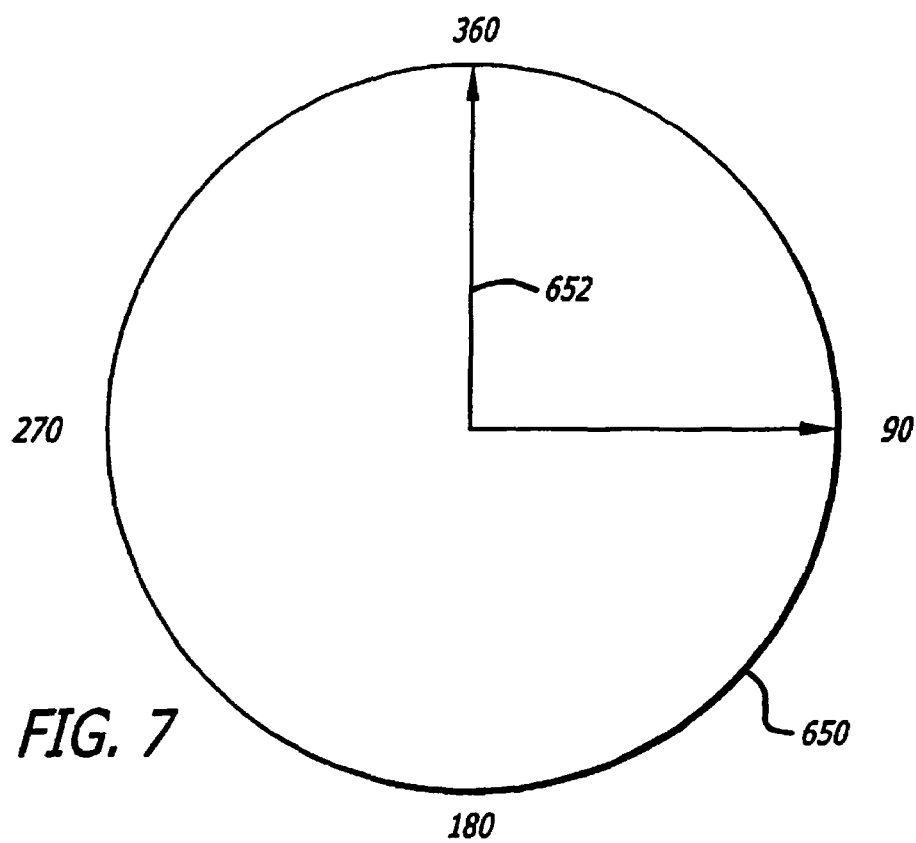
FIG. 7 is a schematic view of a section of a colon showing the drawing of a ray from a luminal center point to the wall of the colon.
Figure 8:
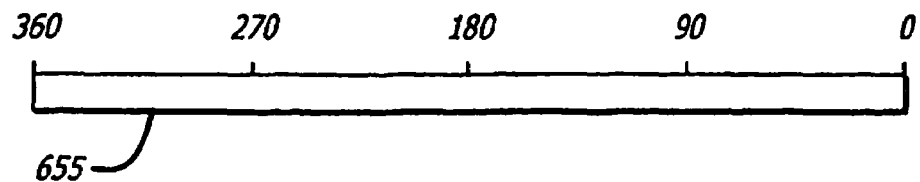
FIG. 8 is a side view of a flattened section of the colon section of FIG. 7.
Figure 9:
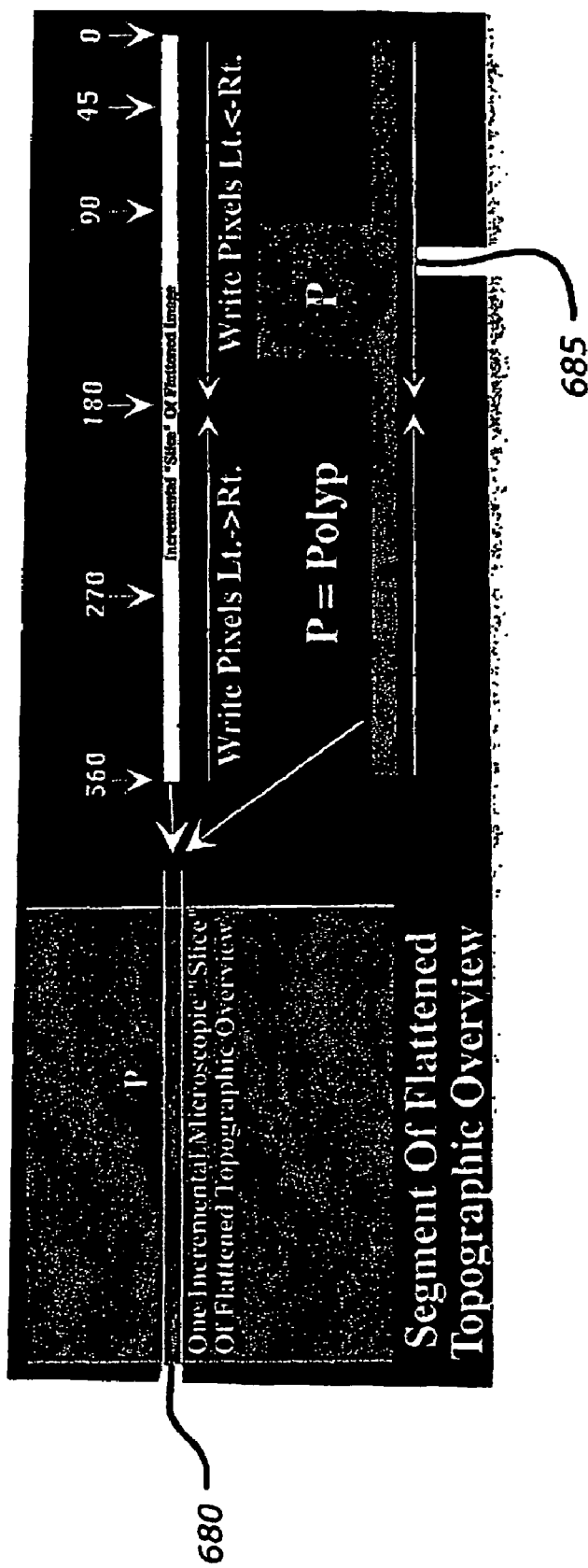
FIG. 9 is a graphical display showing the relationship of a flattened section and an overhead view of a section of the colon.

FIGS. 7-9 illustrate the general principles of the flattening process. As shown in FIG. 7, the colon 650 is a tubular structure having an interior and an exterior defined by a wall. For the purposes of explanation only, the tubular structure of the colon can be thought of as a wall that begins at position zero (not shown) that extends clockwise around FIG. 7 for 360 degrees.

FIG. 8 depicts a slice of colon wall 655 that has been taken at a desired location. As shown in FIG. 8 the flattened colon wall extends from zero degrees to 360 degrees; the flattened image is formed by unwrapping the wall of the colon (FIG. 7). The width of slice 655 may be any width desired by the user, but typically represents a 1 mm wide section of the colon.

FIG. 9 shows this relationship in more detail. A slice 680 of the colon is converted into a flattened image 685. The edge of polyp "P" just intrudes upon slice 685, and can be seen from a view that sets the observers viewpoint directly overhead. This allows smaller structures such as polyps or other abnormalities to be viewed when they otherwise would be hidden by protruding structures of the colon, such as Haustral ridges.

The process used to render flattened slices of the colon will now be described with references to FIGS. 7-10. As described previously, the first step in the overall display process is loading a three-dimensional volume or a series of two-dimensional images that are used to generate a three-dimensional volume into the memory of the computer or processor that is operating in accordance with a software program embodying the principles of the present invention. As described above with reference to FIG. 3, using the multi-planar views of the data set that are displayed by the program, a user of the program defines a starting point, typically near the anus or rectal area, of a pathway that extends through the colon, defining a fly by wire pathway through the luminal center of the colon. The identified points may also be used to identify key frames, which may be stacked to form the three-dimensional volume. In some embodiments, the program includes a sub-process or sub-processes that automatically define a directional vector and curved pathway between the point. In other embodiments, the program provides the user with the ability to automatically center the fly by wire point and to automatically advance the position along the fly by wire pathway. Once the fly by wire pathway has been completed and saved, the same data may be further processed to create a flattened volume. Alternatively, additional processing of the data may be performed to fine tune, optimize and/or smooth the fly by wire pathway.

The flattening process typically begins with a pre-sampling analysis of the data in order to determine the length of the fly by wire pathway, from which the height of the flattened image may be determined. This pre-sampling process is not absolutely necessary, and may be omitted without departing from the principles of the present invention. The pre-sampling process moves the camera/user viewpoint along the fly by wire pathway. At each point or step along the pathway, the camera is rotated 90 degrees about the Y-axis to face the colon wall. Next, the sample is rotated 360 degrees about the original Z-axis, typically in 5 degree increments during the pre-sampling round to reduce analysis time. At each step of rotation, a ray is projected into the colon wall, and the distance to the wall is measured. The average distance measured is used to determine the colon radius at the particular point in the fly by wire pathway. The distance along the fly by wire pathway is then incremented, and the process is repeated.

After the pre-sampling analysis, an image buffer may be created. The height of the image buffer is determined by the length of the fly by wire pathway through the colon. The width of the image buffer is typically 360 to account for the full 360 degree rotation used to retrace the colon walls.

After the image buffer has been created, the process may be continued to generate the final flattened image. The flattened final image is created by once again stepping through the fly by wire pathway. At each step along the fly by wire pathway, the camera is rotated 90 degrees about the Y-axis to face the colon wall. Next, the camera (or virtual observer's viewpoint) is rotated 180 degrees, in 1 degree increments during final flattened image generation, about the original Z-axis. At each rotation a ray is projected into the colon wall. The ray tracing or projection process occurs by incrementing the camera position by approximately one voxel along the z-vector towards the lumen wall. While a one voxel step is described here, steps of other lengths, or multiple voxels, may also be used. In each step, the opacity of the given voxel is determined by comparing the value of the voxel found at the position of the step with an opacity table that is defined by the user. If the voxel that is being stepped through is not air, which is typically defined as zero in the opacity table, its value is added to a voxel value counter based on the weight of its opacity, relative to a pre-defined tolerance. It will be understood that while some voxels are transparent, they affect the image, but have very little relative weight. Once the pre-defined tolerance, which is determined by the user depending on the resolution and contrast, or other windowing parameters selected to optimize the image, has been exceeded, the cumulative voxel value is written to the flattened image buffer.

Typically, the first voxel drawn uses the last vertical line in the flattened image buffer. In this case, the image buffer y offset is the height of the flattened image buffer minus one. The image buffer x offset would then be 180. As shown in FIG. 9, the flattened image is actually drawn into the image buffer starting at zero degrees and rotating to 180 degrees. When a 180 degree rotation has been completed, the camera is reset to its original viewpoint facing the colon wall and the process is repeated by rotating the camera 180 degrees in the opposite direction.

The image buffer offset is reset to 180 and incremented at each rotation since the right side of that horizontal line of the image is drawn first. When the first horizontal line in the flattened image buffer has been drawn, the y-offset of the flattened image buffer is decremented to draw the next row down. The process is continued, stepping forward along the fly by wire pathway and repeating the flattening process at each incremental step along the fly by wire pathway until a composite flattened view of has been drawn. Once the flattened image is completed, it is stored to disk and may then be displayed in a separate window, as depicted in FIG. 4.

Figure 10:
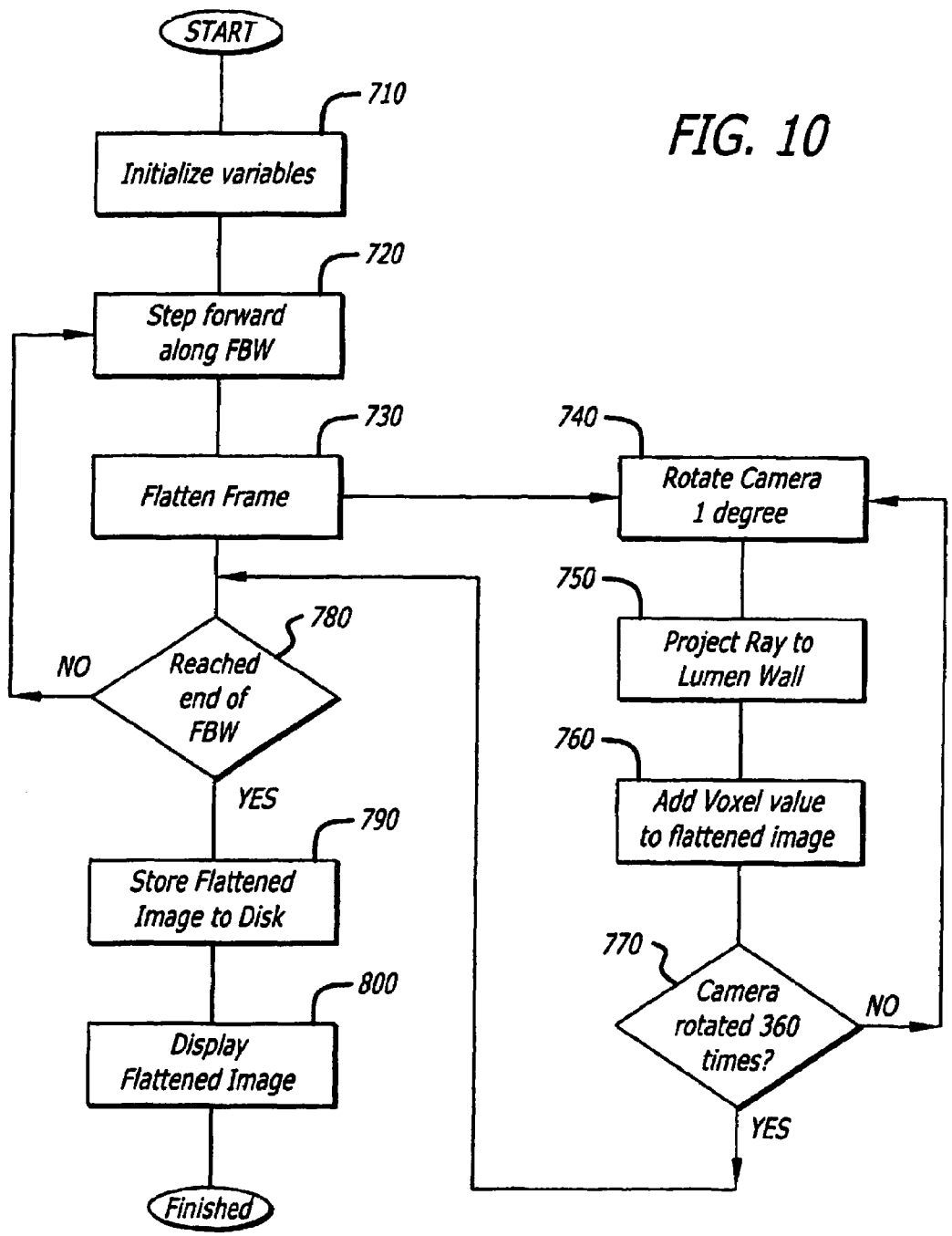
FIG. 10 is a flowchart representing the steps involved in flattening a three-dimensional image of a colon section.

FIG. 10 provides a generalized flow chart illustrating the above described flattening process. As stated previously, the first step in the flattening process is to initialize variables and set up appropriate buffers and look up tables that are used by the process, as indicated in box 710. The process of initializing variables in box 710 also includes picking a starting point along the fly by wire pathway.

Once variables have been initialized and the starting point of the fly by wire pathway has been selected, the process increments one step forward along the fly by wire pathway. The length of the incremental step is user definable, and is generally in the range of 1.0-2.0 mm. Once the first step forward along the fly by wire pathway has been accomplished in box 720, the flattened frame sub-process 730 is executed.

As previously stated, the camera, which represents the user's viewpoint, is rotated one degree in box 740. A ray is projected to the lumen wall in box 750, as is shown by ray 652 in FIG. 7. (While ray 652 is shown pointing to 360 degrees in FIG. 7, the ray pointing to 1 degree, the position of the first increment, has been omitted for clarity, but its position will be readily understood by a skilled person). Once the ray has been projected to the lumen wall, a voxel value is added to a flattened image buffer, as in box 760. As previously described, the processor tests the opacity value of the voxel along the length of the ray until it determines an opacity value that is greater than zero, indicating that the ray has encountered the inner surface of the colon wall.

Once the voxel value has been added to the flattened image, as in box 760, the processor determines whether the camera has been rotated 360 degrees. If the camera has not been rotated 360 degrees, the program branches back to box 740, where the camera is rotated one degree and the processes of boxes 750 and 760 are repeated. If the camera has been rotated 360 degrees, the flattened frame process has been completed for that point on the fly by wire pathway and the process branches back to box 780. In box 780, the program determines whether or not the end of the fly by wire pathway has been reached. If the end of the fly by wire pathway has not been reached, the process branches back to 720, wherein the location along the fly by wire pathway is incremented one unit (which may be, for example, 1.0 mm). The process is repeated for each incremental step until the entire length, or selected portion, or the fly by wire pathway, has been processed. Once the incremental step forward has been executed in box 720, the process then encounters the flattened frame sub-process 730 again, and repeats that as necessary. If it is determined that the end of the fly by wire pathway has been reached in box 780, the flattened image is stored to disk or other appropriate storage media in box 790, and then the flattened image is displayed in box 800. An example of the display of the flattened image synchronized with other views of the colon is depicted in the view titled "Variable Width Flattened View" shown in FIG. 4. It will be understood that the file containing the flattened view data may be played like a movie, that is it may be displayed showing forward or backward flight through the virtual colon, to the provide the user with the sensation of flying over the surface of the colon, much like an aircraft flight simulation program provides the sensation of flying over a simulated terrain. In the case of the present invention, the terrain is the surface of the colon.

Each horizontal line in a flattened image is linked to a three-dimensional position in the acquired colon volume data set. Since the flattened image was created by stepping along a fly by wire pathway through the volume, the user can jump back to the exact place in the volume from a given position in a flattened image. Vertical position (from rectum to cecum) in the flattened image provides the three-dimensional position along the fly by wire pathway in the center of the lumen of the colon.

Using a horizontal position from the flattened image, a three-dimensional position on the lumen wall may be obtained. This value may be used to rotate the camera to the angle that was used to project a ray to create that pixel in the flattened image. From this position, a ray is projected just as in the flattening process to move the camera to the actual position in the three-dimensional volume. Projecting the ray in this manner, a sub-surface view of the colon wall may be generated by allowing the ray to continue to increment into the colon wall through solid tissue.

Generating a sub-surface view of the colon wall in this manner allows for the assessment of mucosal and submucosal wall thickness for areas of abnormality. For example, such a localized abnormality may be one of the roughly 7 percent of colorectal cancers that arise not from slow growing visible polyps, but from fast growing, aggressive flat tumors which are difficult to detect by any screening procedure. Moreover, assessing wall thickness in a manner independent of prior window width and window level settings, minimizes the possibility for missing constricting tumors which can be overlooked using only three-dimensional endoluminal views or two-dimensional multiplanar views that rely on narrow high contrast window settings to view and analyze CT image data.

Where narrowed colonic segments are observed, the cause may be either inadequate air insufflation, spasm, or some structure compressing the lumen either intrinsic to the colon wall, such as inflammatory bowel disease or a tumor, or extrinsic to the colon, such as an adjacent organ or mass in the immediate pericolonic vicinity. Using typical "lung" window settings, it is very difficult, if not impossible, for an observer to determine whether or not the narrowing is due to a standing artifact, such as inadequate air insufflation, or some underlying disease or structural abnormality.

The advantages of this approach readily seen with reference to the variable width flattened view depicted in FIG. 4. Here, reference line 210 is set in a portion of a section of the colon that has been restricted by a circumferential tumor. As will be apparent to those skilled in the art of reading images of the sort depicted in FIG. 4, the circumferential tumor would not readily be seen from the three-dimensional endoluminal view present in FIG. 4. If the mag axial, mag sagittal, or mag coronal images also shown in FIG. 4 had been presented using traditional "lung" windows (in FIG. 4 these images are properly windowed) these the constricting tumor would also have been missed. However, the sub-surface view, shows a thickened rind of colon wall that is indicative of an advanced malignant colon tumor.

Figure 11:
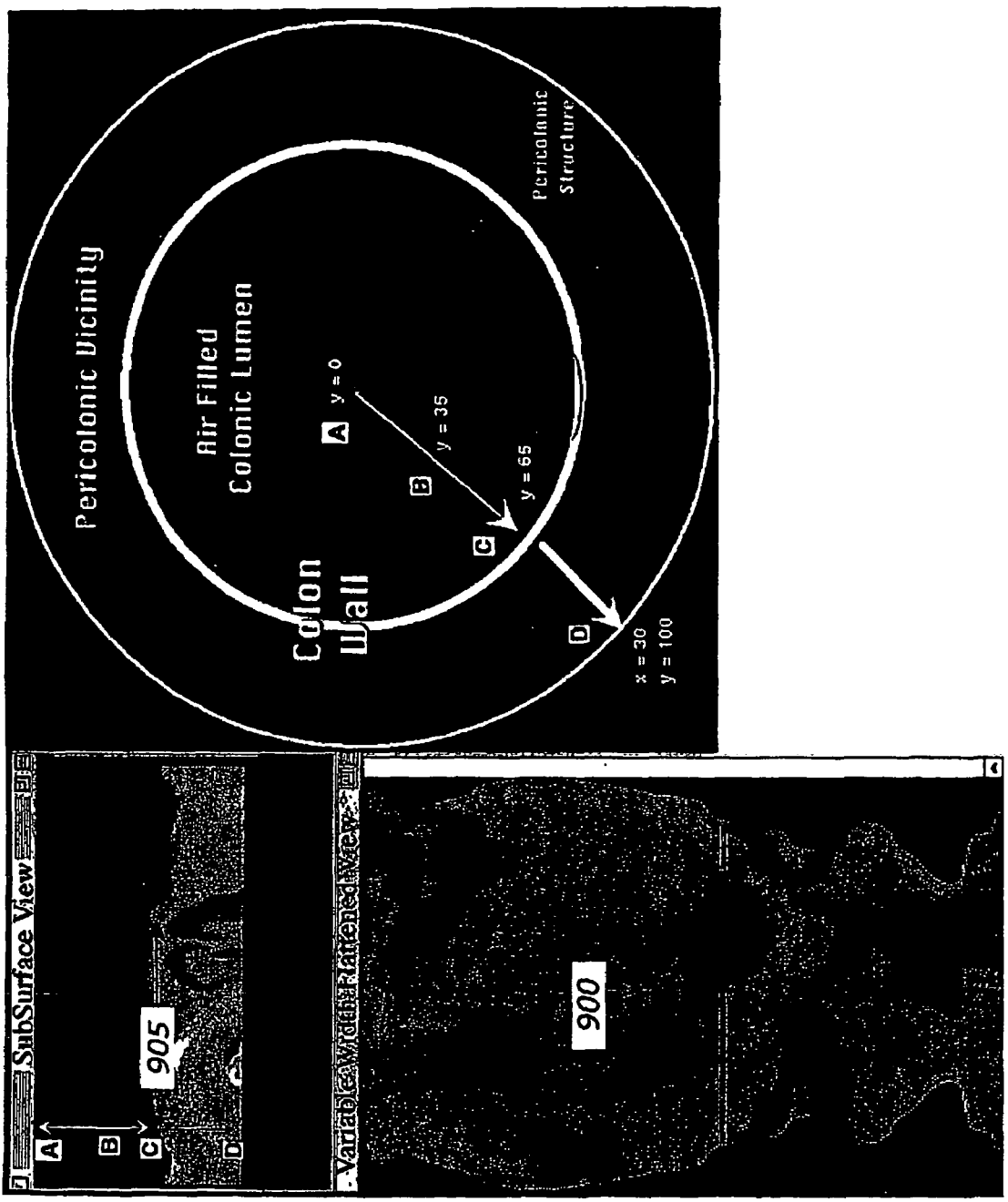
FIG. 11 is a composite view of a cross-sectional view of a colon including points representing the stepping of a ray from a luminal center point to and through the colon wall, coordinated with two views representative of the display of images rendered using the methods of the present invention.

The process for rendering the sub-surface view of the volume data set will now be described with reference to FIGS. 11 and 12. FIG. 11 includes an illustration of how the sub-surface structure is determined by stepping the ray through the colon wall and into the pericolonic structure. Also included in FIG. 11 are a variable width flattened view with a sub-surface view of a particular section of the variable width flattened view. The sub-surface view is keyed to the display of the graphic illustrating the retracing process.

Figure 12:
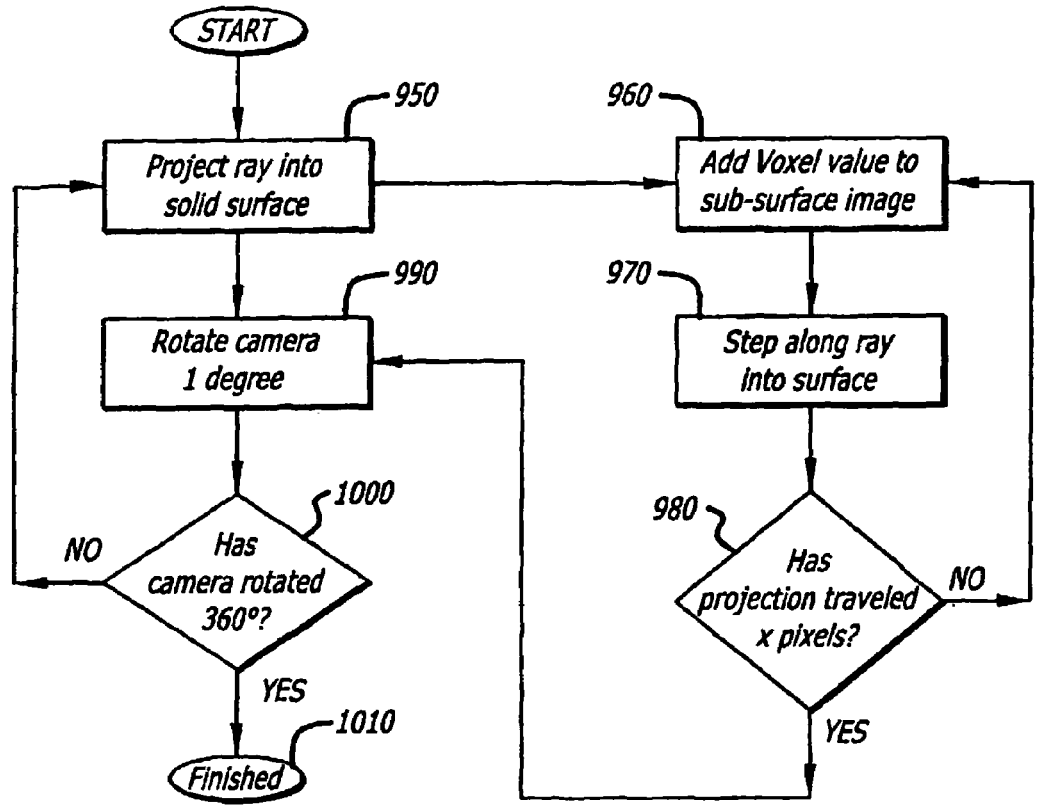
FIG. 12 is a flowchart representing the steps involved in calculating and displaying a subsurface view of a section of a colon wall.

FIG. 12 is a generalized flow diagram showing the various steps included in rendering the sub-surface view of the volume set for a selected scan line of a flattened image.

Once a user has selected a location within the variable width flattened view, as indicated by arrow 900 in FIG. 11, the process used to generate the sub-surface view begins. A ray is projected into the lumen wall, as in box 950. In projecting the ray into the lumen wall, the ray is stepped x voxels along the vector into wall, as in box 970. The program then determines whether or not the projection has traveled x pixels, the value for which is chosen by the user, in box 980. If the projection has not traveled x pixels, the process branches back to box 960, and is repeated. If it is determined that the projection has traveled x pixels, for example, 90 pixels, the program branches to box 990, where the camera (or viewpoint) is rotated or shifted one degree.

A pictorial example of this process is shown better in FIG. 11. Here, the starting point of the ray is depicted by point A where y, the distance along the Y-axis, is arbitrarily set equal to zero. This point is typically selected to be the center of the air filled colonical lumen. The processor then projects the ray outwards towards the colon wall. In general, the ray will be projected from the center point a distance of typically 90 pixels, although other projection distances may be selected by the user for this analysis. Projecting the ray 90 pixels, or some other desired greater distance, results in the ray projecting into the wall, allowing the internal structure of the wall, and also structures on both sides of the wall, to be imaged. As the ray is projected, voxel values are calculated based upon an opacity table in box 990 for any structures encountered by the ray and are added to the sub-surface image buffer in step 1000.

As shown in the diagram in FIG. 11, the ray continues to be incrementally projected to point B, where y equals 35, then to point C where y equals 65. It should be understood that the units of y may not be an actual measurement of distance, although that is possible. Alternatively, the units of y may indicate a proportional step determined from desired analysis distance starting from the center point and extending into the wall a desired distance.

At position C where y equals 65, the ray encounters the wall of the colon. The ray is then allowed to project a further distance, to point D, where y equals 100, thus rendering an image that includes not only the thickness of the colon wall, but also some distance into the pericolonic vicinity.

This stepwise process is also observable in the sub-surface view depicted in FIG. 11. In the sub-surface view, point A represents the starting point in the center of the air filled colonic lumen. Point C represents the inner surface of the colon wall. As the ray is projected to point D in the subsurface view, the structure of the colon wall as well as some of the pericolonic structure is viewable. In this manner, an abnormality, located on the surface of the colon wall, indicated by arrow 900, which is otherwise extremely difficult to differentiate from the background of the flattened colon can easily be seen in the sub-surface view, as indicated by arrow 905.

The subsurface view, in coordination with the flattened view, provides the user with two different ways of viewing the colon. The flattened view may be likened to a stretched aeronautical surface topography map of the colon that contains surface elevation data of structures, like polyps, that extend from the wall of the colon. The subsurface view, in contrast, provides a view of the structure above and below the surface of the colonic wall. Thus, the sub-surface view generated in accordance with the principles of the present invention, provides substantial advantages to the user in providing the ability to observe abnormalities or disease related artifacts that would otherwise not be viewable in any other view presently available for analysis of CT scan data.

Returning again to FIG. 12, after the projection has traveled x pixels, the process returns to box 990, where the camera, or user viewpoint is rotated 1 degree. The process then determines in box 1000 whether the camera has been rotated 360 times, thus, rotating about the entire inner surface of the colon wall. If the camera has been rotated 360 times, the program branches to box 1010 and the sub-surface volume is displayed. If the camera has not been rotated 360 times, the program branches back to box 950, where the projection of the ray into the lumen wall is repeated until the entire image has been rendered.

The isotropic data sets generated using the methods of the present invention may also be used as input for a computer aided diagnostic system. In such a system, the data sets may be further processed using pattern recognition software. In this manner, abnormalities may be identified by computation of three-dimensional features that identify polyps or other abnormal structure. Various techniques, such as applying quadratic discriminant analysis, hysteresis thresholding and fuzzy clustering may be used to reduce the occurrence of false positive identification of abnormal structures.

Figure 13:
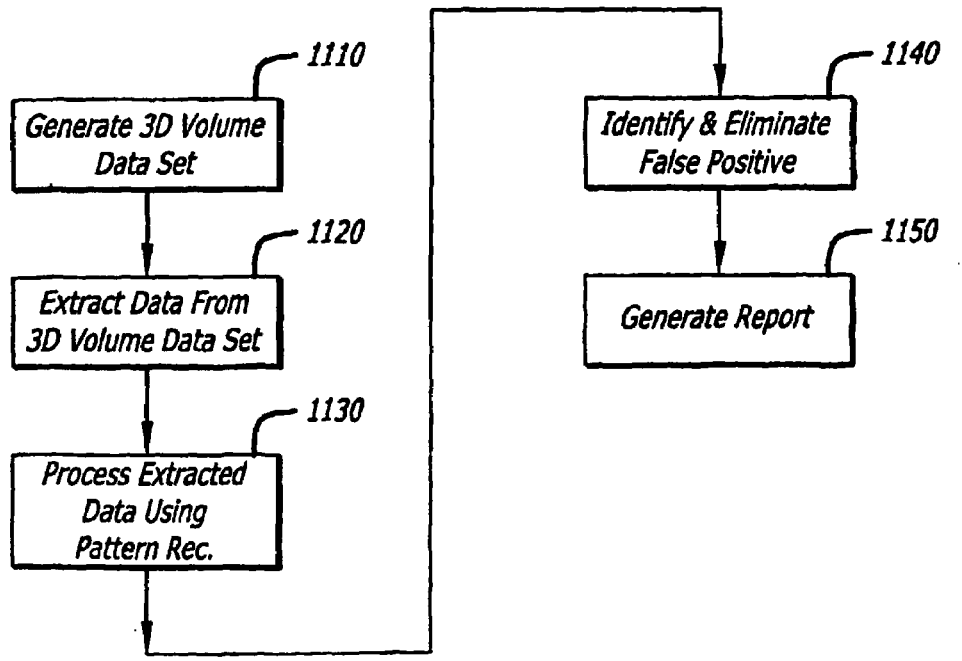
FIG. 13 is a flowchart representing an embodiment of the present invention that includes computer aided diagnosis performed using pattern recognition software analysis of the stored data generated using aspects of the present invention.

FIG. 13 is a flowchart describing in general the steps used to render a diagnosis using pattern recognition to identify structural abnormalities in a colon. Using the methods set forth above, the CT scan data is processed and three-dimensional volume dates sets are generated in box 1110. Data representing the entire colon, or a selected portion of the colon may be extracted from the three-dimensional volume data set, as indicated in box 1120.

The extracted data set is then processed in box 1130 using a pattern recognition program that has been designed to compare three-dimensional features of the volume data set with a set of pre-determined geometrical shapes that have been determined to be representative of the geometric shape of abnormalities found in the colon, such as polyps. The program generates a listing of abnormalities, including the coordinates within the three-dimensional data base where they are located, which may be used to visually assess the abnormality to determine whether the abnormality has been properly identified, or if it is simply a structural feature that resembles an abnormality, but which is otherwise benign. The data representing the abnormality may also be extracted from the data set and stored separately for further analysis.

Although not necessary, it may be desirable to further process, as indicated in box 1140, the three-dimensional data set to further define the identification of the abnormal structures to reduce the occurrence of false positives, that is, structures tagged as abnormal but which are in actuality benign. The further processing may be carried on the entire data set, or an extracted data set containing volume data representative of the area of the colon surrounding the location of the identified abnormality. Such further processing includes applying various techniques known in the art, such as quadratic discriminant analysis, hysteresis thresholding and fuzzy clustering to the data to improve the identification of abnormalities and reduce the occurrence of false positives.

Once all processing is completed, a report is generated in box 1150 which is communicated to a surgeon and/or the patient's physician. This report may contain various information concerning the scan and the abnormalities identified during the scan, and is intended to aid the physician in diagnosis and treatment of the patient.

Figure 14:
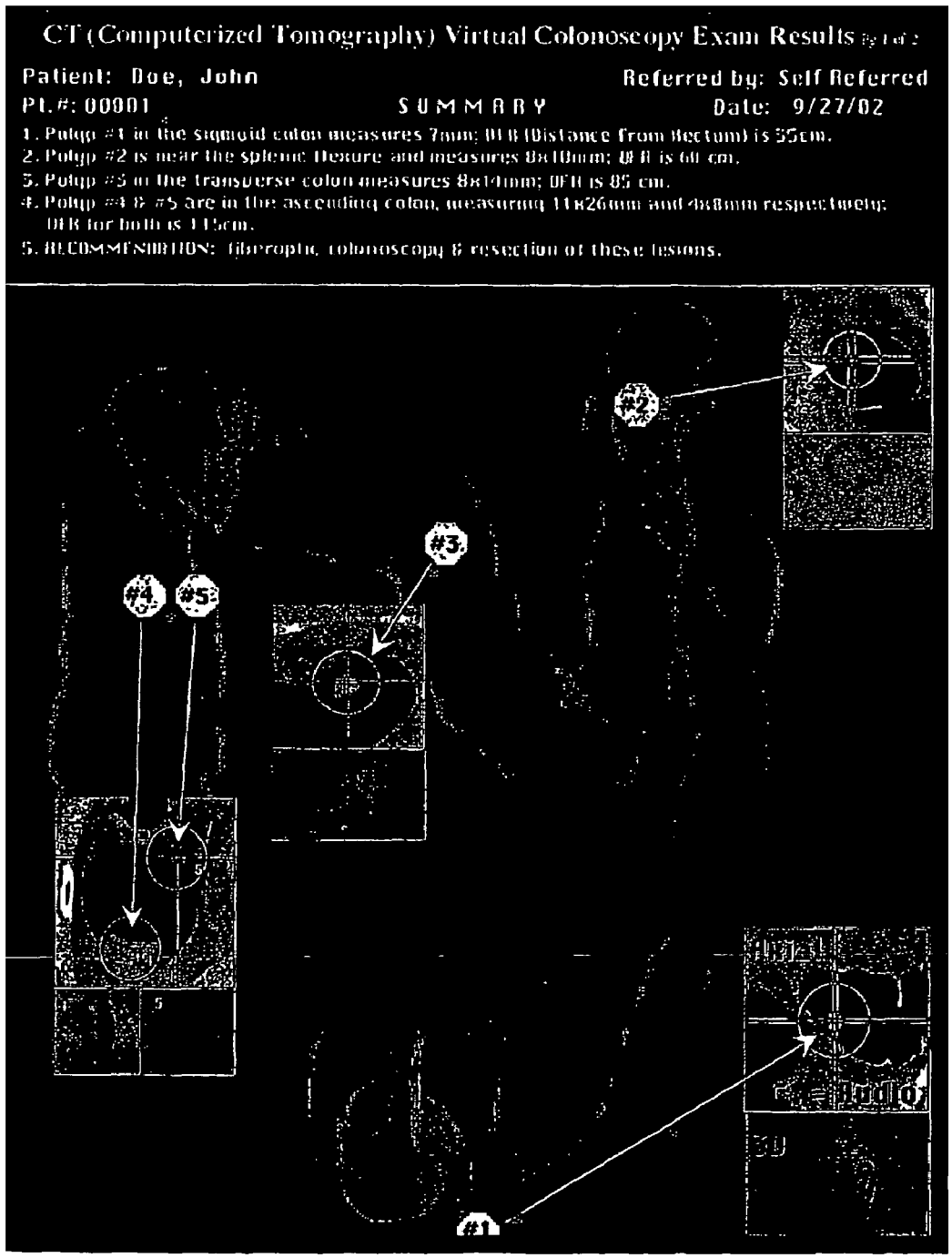
FIG. 14 is a graphical representation of one embodiment of a report that may be generated using the system and methods of the present invention.

An example of such a report is shown in FIGS. 14 and 15. FIG. 14 depicts a view of entire colon of a patient, with particular segments identified. FIG. 15 shows a computer generated report keyed to the segments identified in FIG. 14. These reports are suitable for use by a physician, and may also be given directly to a patient by the physician to assist the patient's understanding of his or her condition, and any treatment that may be suggested by the physician.

A particularly advantageous application of the system and methods various embodiments of the present invention is the ability to automatically, or semi- automatically, render volume data sets, diagnose abnormalities and generate reports using relatively inexpensive computers and displays, as well as the ability to do so using data that is communicated to a remote analysis site from one or more scanning centers. For example, one embodiment of the present invention contemplates a centralized system or analyzing large volumes of CT scan data communicated to a central analysis location. Such a system would allow the scanning centers to scan patients without being burdened with the overhead of having to also analyze the data and generate reports. For example, a single analysis center using the system and method of the present invention would receive and analyze CT scan data from 100 or more scanning centers.

Once the data is received by the analysis center, the data is either processed by the center, or alternatively, could be sent to secondary centers for processing. If the data is sent to secondary centers, the reports and/or processed volume data sets generated by the secondary center are sent back to the analysis center for communication either to the originating scanning center or to surgeons and/or physicians identified by the scanning center. Such a system also provides for analysis of the data using skilled technologists who report their findings to radiologists, who then may provide a report containing their opinion after reading the scan data and their suggestions for treatment which is then communicated to the appropriate surgeon or physician.

It will be understood by those skilled in the art that while the system and methods of the present invention have been described with reference to the imaging of a patient's colon, the various embodiments of the present invention are equally applicable to the scanning and analysis of other structures of the body. For example, the flattening and subsurface methods described are equally useful to image and analyze any tubular structure of the body, such as the trachea, esophagus and the like.

While specific embodiments of the invention have been illustrated and described, it will be apparent that various modifications can be made without departing from the spirit and scope of the invention. Accordingly, it is therefore intended that the invention be limited, except as by the appended claims.

```
/*------------------------------*/
1) Rotate to Coronal Anterior View for start
      gCameraViewAngle.x = 90;
      gCameraViewAngle.y = 0;
      gCameraViewAngle.z = 0;
2) Then rotate 360 degrees about z-axis sampling voxels as we go
3) Next step forward 1 voxel and repeat step 2
*/
char   FlattenFrameNEW( )
{long              maxDegrees, z, i;
 long              voxelValue;
 Point3dDouble     tempPosition, startPosition;
 Uint32                        *zOffsetTable;
 Uint32                        *yOffsetTable;
 Uint8                         *volBuffer;
 Uint8                         *sliceBuffer;
 C3dVolume                     *volume;
 Point3dDouble     tempRotAngle, theRotAngle;
      if (gUseVariableWidthFlattening)
                 return FlattenFrameVW( );
// Get some globals from the flattened volume
      volume = gFlattenedView->f3dVolume;
      if (volume != NULL)
      {
                 volBuffer = volume->f3dVolumeBuffer;
                 zOffsetTable = (Uint32*) volume->fZoffsetTable;
                 yOffsetTable = (Uint32*) volume->fYoffsetTable;
      gDestVolIndex.x = 359;
      //Reset the Vectors;
      Point3dLongToDouble(&gxVectorDouble,gxVectorLong);
      Point3dLongToDouble(&gyVectorDouble,gyVectorLong);
      Point3dLongToDouble(&gzVectorDouble,gzVectorLong);
///////////
      theRotAngle = gzVectorDouble;
      gzVectorDouble = gxVectorDouble;
      gxVectorDouble = theRotAngle;
      theRotAngle.x = -gxVectorDouble.x;
      theRotAngle.y = gxVectorDouble.y;
      theRotAngle.z = -gxVectorDouble.z;
      tempRotAngle = theRotAngle;
      maxDegrees = 180;
      SaveViewVectorsDouble( );
      gDestVolIndex.x = 180;       // Start at center for variable width flattening
      for (i = 0; i < maxDegrees; i +=1 )
      {         Point3dLongToDouble(&startPosition,gCameraPosition);
                tempPosition = startPosition;
                voxelValue =
```

-continued

```
SamplePixelFastDouble2(tempPosition,&gzVectorDouble,gSlopFactor,0);
                Update3dVectorsDoubleNEW(theRotAngle);    // rotate 360 degrees
about z-axis 1 degree at a time
                gDestVolIndex.x--;}
//**********
    RestoreViewVectorsDouble( );
    theRotAngle.x = -theRotAngle.x;
    theRotAngle.y = -theRotAngle.y;
    theRotAngle.z = -theRotAngle.z;
    gDestVolIndex.x = 180;    // Start at center for variable width flattening
    for (i = 0; i < maxDegrees; i +=1 )
    {
                Point3dLongToDouble(&startPosition,gCameraPosition);
                tempPosition = startPosition;
                voxelValue =
SamplePixelFastDouble2(tempPosition,&gzVectorDouble,gSlopFactor,0);
                Update3dVectorsDoubleNEW(theRotAngle);    // rotate 360 degrees
about z-axis 1 degree at a time
                gDestVolIndex.x++;
    }
    if (gDestVolIndex.z >= 0)
    {
                *(gFlattenRefLineBuffer + gDestVolIndex.z) =
gCameraPositionDouble;
    }
    gColonFrameIndex++;
    gDestVolIndex.z--;
    return TRUE;
}
/*--------------------------------*/
long    SampleXRayFastDouble2(Point3dDouble tempVectorIndex,Point3dDouble
*vectorStep,short slopFactor,long cpuIndex)
{
Uint8           *theBuffer;
long            *transparencyValue;
long            *opacityValue;
 Uint32                *zOffsetTable;
 Uint32                *yOffsetTable;
short           theCount;
short           voxValue;
Uint32              volOffset;
Uint8           theValue;
long            transpFactor;
long            grossTranspFactor;
Uint32              finalIndexValue;
Uint32              volumeBufferMax;
long            volumeOffsetMax;
long            xCount, yCount, zCount;
long            tempIndex;
Point3dDouble               tempVolumeSizeMin, tempVolumeSizeMax;
register double             tempVectorStepx, tempVectorStepy, tempVectorStepz;
Uint8           *overViewImage;
Point3dDouble tempPosition, startPosition;
char            firstVoxel = TRUE;
double          vertOverSampling;
    finalIndexValue = 0;
    grossTranspFactor = 0;
    theBuffer = g3dVolumeBufferPtr;
/////////
    zOffsetTable = (Uint32*) gZoffsetTablePtr;
    yOffsetTable = (Uint32*) gYoffsetTablePtr;
    transparencyValue = (long*) &gTransparencyValue[0];
    opacityValue = (long*) &gOpacityValue[0];
#define VERT_OVERSAMPLE
#ifdef VERT_OVERSAMPLE
/////////////////
// Vertical oversampling
    vertOverSampling = (double) gSubSurfaceDepth/128.0;
    tempVectorStepx = vectorStep->x * vertOverSampling;
    tempVectorStepy = vectorStep->y * vertOverSampling;
    tempVectorStepz = vectorStep->z * vertOverSampling;
#else
    tempVectorStepx = vectorStep->x;
    tempVectorStepy = vectorStep->y;
    tempVectorStepz = vectorStep->z;
#endif
    volumeBufferMax = gVolumeBufferMax;
    volumeOffsetMax = g3dVolumeBufferSize;
    tempVolumeSizeMax = gTempVolumeSizeMax;
```

```
///////////////////
// The loop
    theCount = min(gViewDepth,200);
    startPosition = tempVectorIndex;
    do
    {
            tempIndex = tempVectorIndex.z;
            volOffset = *(zOffsetTable+(tempIndex));
            tempIndex = tempVectorIndex.y;
            volOffset += *(yOffsetTable+(tempIndex));
            volOffset += tempVectorIndex.x;
            if (volOffset >= 0 && volOffset < volumeOffsetMax)
            {
                    theValue = *(theBuffer+volOffset);
                    transpFactor = transparencyValue[theValue];
                    if (transpFact != 0)
                    {
                            {
                            grossTranspFactor += transpFactor;
                            if (grossTranspFactor >= 0x1000)
                            {
                                    if (firstVoxel)
                                    {
                                            tempPosition = tempVectorIndex;
                                            tempPosition.x -= startPosition.x;
                                            tempPosition.y -= startPosition.y;
                                            tempPosition.z -= startPosition.z;
                                            yCount =
quickSquareRoot((tempPosition.x*tempPosition.x)+(tempPosition.y*tempPosition.
y)+(tempPosition.z*tempPosition.z));
                                            firstVoxel = FALSE;
                                    }
                                    else
                                            yCount++;
                                    if(yCount < 0 || yCount >= 128) //
VERT_OVERSAMPLE
                                    {
                                    //      DebugThis(4812);
                                            theCount = 0;
                                            break;
                                    }
                                    overViewImage = gXRayImage;
                                    overViewImage += yCount * gXRayRowBytes;
                                    overViewImage += gDestVolIndex.x;
                                    *overViewImage = theValue;
                                    finalIndexValue = 0;
                                    grossTranspFactor = 0x10000;          //just in case
of overflow
                            }
                            finalIndexValue += opacityValue[theValue];
                            }
                    }
            }
            {
            tempVectorIndex.x += tempVectorStepx;
            tempVectorIndex.y += tempVectorStepy;
            tempVectorIndex.z += tempVectorStepz;
            }
    } while (theCount-- > 0);
    return((long) theValue);
}
/*-----------------------------*/
/*
            Take an "xray" view of a slice from the flattened image
    Same code as one flatten sliver (from one FBW center point)
    Instead of stopping at surface walls dig below to a certain depth
*/
char    XRayFrame( )
{
long                    maxDegrees, z, i;
CMainView               *oldMainView;
long                    voxelValue;
Point3dDouble           tempPosition, startPosition;
Uint32                      *zOffsetTable;
Uint32                      *yOffsetTable;
Uint8                   *volBuffer;
Uint8                   *sliceBuffer;
Uint32                      volOffset;
long                    rayDistance, tempIndex;
```

-continued

```
C3dVolume                    *volume;
Point3dDouble                tempRotAngle, theRotAngle;
    SaveViewVectors( );
    if(!gVirtualColonView->fVCMovie->fPlayMovie)
    {
            gOverrdeAnimUpdate = TRUE;
            gMakeFlattenedMovie = 10;
            gVirtualColonView->fVCMovie-
>FindFrame(*(gFlattenRefLineBuffer + gRefLineNumber));
            gMakeFlattenedMovie = FALSE;
            gOverrideAnimUpdate = FALSE;
    }
// To set view vectors correctly
//////////////
// Get some globals from the flattened volume
    volume = gFlattenedView->f3dVolume;
    if (volume != NULL)
    {
            volBuffer = volume->f3dVolumeBuffer;
            zOffsetTable = (Uint32*) volume->fZoffsetTable;
            yOffsetTable = (Uint32*) volume->fYoffsetTable;
    }
    gDestVolIndex.x = 359;
//////////
// Reset the vectors
    Point3dLongToDouble(&gxVectorDouble,gxVectorLong);
    Point3dLongToDouble(&gyVectorDouble,gyVectorLong);
    Point3dLongToDouble(&gzVectorDouble,gzVectorLong);
//////////
    theRotAngle = gzVectorDouble;
    gzVectorDouble = gxVectorDouble;
    gxVectorDouble = theRotAngle;
    theRotAngle.x = -gxVectorDouble.x;
    theRotAngle.y = gxVectorDouble.y;
    theRotAngle.z = -gxVectorDouble.z;
    tempRotAngle = theRotAngle;
    Normalize3d(&theRotAngle);
    maxDegrees = 180;
    Save View VectorsDouble( );
    gDestVolIndex.x = 180;   // Start at center for variable width flattening
    for (i = 0; i < maxDegrees; i +=1 )
    {
            Point3dLongToDouble(&startPosition,gCameraPosition);
            tempPosition = startPosition;
            voxelValue =
SampleXRayFastDouble2(tempPosition,&gzVectorDouble,gSlopFactor,0);
            Update3dVectorsDoubleNEW(theRotAngle);       // rotate 360 degrees
about z-axis 1 degree at a time
            gDestVolIndex.x--;
    }
//**********
    RestoreViewVectorsDouble( );
    theRotAngle.x = -theRotAngle.x;
    theRotAngle.y = -theRotAngle.y;
    theRotAngle.z = -theRotAngle.z;
    gDestVolIndex.x = 180; // Start at center for variable width flattening
    for (i = 0; i < maxDegrees; i +=1 )
    {
            Point3dLongToDouble(&startPosition,gCameraPosition);
            tempPosition = startPosition;
            voxelValue =
SampleXRayFastDouble2(tempPosition,&gzVectorDouble,gSlopFactor,0);
            Update3dVectorsDoubleNEW(theRotAngle);       // rotate 360 degrees
about z-axis 1 degree at a time
            gDestVolIndex.x++;
    }
    RestoreViewVectors( );
    return TRUE;
}
```

What is claimed is:

1. A method of rendering a flattened view of a tubular body structure having a lumen defined by a wall, comprising:
   providing a data set containing data representing a plurality of cross-sectional images of a tubular structure of the body taken along a longitudinal axis of the tubular body;
   processing the data set to reconstruct a three-dimensional image of the tubular body;
   identifying a central pathway through a lumen of the three-dimensional image; selecting a starting point along the central pathway;
   projecting a ray from the starting point to the wall, the direction of the ray corresponding to an angle of view;
   calculating a voxel value at the location of the wall;
   storing the voxel value in an image buffer to provide the flattened view;
   shifting the angle of view by one degree in a selected direction, projecting another ray from the starting point to the wall, the direction of the ray corresponding to the shifted angle of view if the angle of view has not been shifted a total of 180 degrees from the initial starting point, calculating a voxel value at the location of the wall and storing the voxel value in the image buffer;
   returning to the starting point if the angle of view has been shifted a total of 180 degrees;
   shifting the angle of view by one degree in a direction opposite from the selected direction, projecting another ray from the starting point to the wall, the direction of the ray corresponding to the shifted angle of view if the angle of view has not been shifted a total of 180 degrees from the initial starting point, calculating a voxel value at the location of the wall and storing the voxel value in the image buffer;
   advancing the starting point along the longitudinal axis of the lumen by a selected value if the angle of view has been shifted a total of 180 degrees from the initial starting point;
   displaying the flattened view of the image.

2. The method of claim 1, further comprising:
   selecting a point along the central pathway;
   processing the data at the selected point and rendering an image of a cross-section of the wall of the tubular structure at the selected point; and
   displaying the image of the cross-section of the wall of the tubular structure.

3. The method of claim 1, further comprising:
   repeating the steps of projecting the ray and storing voxel values in an image buffer until the entire length of the lumen has been processed.

4. The method of claim 1, wherein the tubular structure is a colon.

5. The method of claim 1, further comprising:
   comparing the three-dimensional volume data set to a library of geometrical patterns representative of predetermined abnormalities;
   identifying a structure contained in the three-dimensional volume data set as abnormal if the structure is determined to match at least one of the library of geometrical patterns within a predetermined tolerance.

6. The method of claim 5, further comprising:
   further processing the identified abnormal structure to determine if the identified structure is not abnormal.

7. A method for generating a view of the tissue structures within a thickness dimension of a wall of a tubular structure of a body including tissue adjacent the exterior of the wall, comprising the steps of:
   (a) providing a data set containing data representing a three-dimensional volume representing a tubular structure of the body taken along a longitudinal axis of the tubular body, the tubular body having a lumen defined by a wall;
   (b) selecting a starting point along a central pathway disposed along the longitudinal axis of the tubular body;
   (c) projecting a ray towards the wall a selected distance by stepping towards the wall along the ray from the staffing point, the distance selected such that the ray steps into and through the thickness of the wall;
   (d) calculating a voxel value at the location of each step of the ray;
   (e) adding the voxel value to an image buffer to provide a subsurface volume image;
   (f) incrementing the angular projection of the ray one degree in a selected direction when the selected distance is reached;
   (g) repeating steps (c) through (f) until the angular projection of the ray has been incremented a total of 180 degrees in the selected direction and then returning to the starting point;
   (h) repeating steps (c) through (f), where the selected direction is a direction opposite to the selected direction of step (f) until the angular projection of the ray has been incremented a total of 180 degrees in the opposite direction;
   (i) advancing the staffing point along the central pathway a selected distance; and
   (j) repeating steps (c) through (i) until a desired section of the central pathway is imaged;
   (k) displaying the subsurface volume image representing tissue structure present within the thickness dimension of the wall.

8. The method of claim 7, wherein the tubular structure in a colon.

9. The method of claim 7, further comprising:
   comparing the three-dimensional volume data set to a library of geometrical patterns representative of predetermined abnormalities;
   identifying a structure contained in the three-dimensional volume data set as abnormal if the structure is determined to match at least one of the library of geometrical patterns within a predetermined tolerance.

10. The method of claim 9, further comprising:
    further processing the identified abnormal structure to determine if the identified structure is not abnormal.

* * * * *

UNITED STATES PATENT AND TRADEMARK OFFICE
CERTIFICATE OF CORRECTION

| | |
|---|---|
| PATENT NO. | : 7,640,050 B2 |
| APPLICATION NO. | : 10/507337 |
| DATED | : December 29, 2009 |
| INVENTOR(S) | : William V. Glenn, Jr. et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 847 days.

Column 5, line 49, after "of" insert --the--.

Column 8, line 29, after "that" delete "allows".

Column 12,
line 45, after "also" insert --be--.
line 50, after "whether" delete "relative" and insert instead --relatively--.

Column 13, line 37, delete "it" and insert instead --is--.

Column 14, line 6, after "used" delete "to".

Column 18,
line 45, after "approach" insert --are--.
line 55, after "windowed)" delete "these".

Column 21,
line 8, after "methods" insert --of--.
line 15, after "system" delete "or" and insert instead --for--.

Column 30,
line 37, after "advancing the" delete "staffing" and insert instead --starting--.
line 44, after "structure" delete "in" and insert instead --is--.

Signed and Sealed this

Fourteenth Day of December, 2010

David J. Kappos
*Director of the United States Patent and Trademark Office*